US006620413B1

(12) United States Patent
DeSauvage et al.

(10) Patent No.: US 6,620,413 B1
(45) Date of Patent: *Sep. 16, 2003

(54) OB PROTEIN-POLYMER CHIMERAS

(75) Inventors: Frederic DeSauvage, Foster City, CA (US); Nancy Levin, Newbury Park, CA (US); Richard Vandlen, Hillsborough, CA (US)

(73) Assignee: Genentech, Inc., South San Francisco, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/775,066

(22) Filed: Dec. 27, 1996

Related U.S. Application Data

(60) Provisional application No. 60/040,911, filed on Dec. 27, 1995.

(51) Int. Cl.[7] .................. A61K 39/395; A61K 39/40; A61K 38/00; C07K 1/00
(52) U.S. Cl. .................. 424/178.1; 424/179.1; 514/2; 530/350
(58) Field of Search .................. 530/350; 424/178.1, 424/179.1; 514/2

(56) References Cited

U.S. PATENT DOCUMENTS

| | | | |
|---|---|---|---|
| 5,349,053 A | | 9/1994 | Landolfi |
| 5,428,130 A | * | 6/1995 | Capon et al. |
| 5,521,283 A | | 5/1996 | DiMarchi et al. |
| 5,525,705 A | | 6/1996 | DiMarchi et al. |
| 5,532,336 A | | 7/1996 | DiMarchi et al. |
| 5,552,522 A | | 9/1996 | DiMarchi et al. |
| 5,552,523 A | | 9/1996 | Basinski et al. |
| 5,552,524 A | | 9/1996 | Basinski et al. |
| 5,554,727 A | | 9/1996 | Basinski et al. |
| 5,559,208 A | * | 9/1996 | Basinski et al. |
| 5,563,243 A | | 10/1996 | DiMarchi et al. |
| 5,563,244 A | | 10/1996 | DiMarchi et al. |
| 5,563,245 A | | 10/1996 | DiMarchi et al. |
| 5,567,678 A | | 10/1996 | DiMarchi et al. |
| 5,567,803 A | | 10/1996 | Basinski et al. |
| 5,569,743 A | | 10/1996 | DiMarchi et al. |
| 5,569,744 A | | 10/1996 | Basinski et al. |
| 5,574,133 A | | 11/1996 | DiMarchi et al. |
| 5,580,954 A | | 12/1996 | DiMarchi et al. |
| 5,594,101 A | | 1/1997 | Becker et al. |
| 5,594,104 A | | 1/1997 | Basinski et al. |
| 5,605,886 A | | 2/1997 | Basinski et al. |
| 5,614,379 A | | 3/1997 | MacKellar |
| 5,643,748 A | | 7/1997 | Snodgrass et al. |
| 5,691,309 A | | 11/1997 | Basinski et al. |
| 5,698,389 A | | 12/1997 | de la Brousse et al. |
| 5,827,734 A | | 10/1998 | Weigle et al. |
| 5,856,098 A | | 1/1999 | Snodgrass et al. |
| 5,858,967 A | | 1/1999 | Weigle et al. |
| 5,869,610 A | | 2/1999 | Snodgrass et al. |
| 5,882,860 A | | 3/1999 | Snodgrass et al. |
| 5,912,123 A | | 6/1999 | Snodgrass et al. |
| 5,935,810 A | | 8/1999 | Friedman et al. |
| 5,968,779 A | | 10/1999 | Campfield et al. |
| 5,972,621 A | | 10/1999 | Tartaglia et al. |
| 6,001,968 A | * | 12/1999 | Friedman et al. |
| 6,005,080 A | | 12/1999 | Snodgrass et al. |
| 6,025,325 A | * | 2/2000 | Campfield et al. |
| 6,124,439 A | | 9/2000 | Friedman et al. |
| 2002/0037553 A1 | | 3/2002 | Al-Barazanji et al. |

FOREIGN PATENT DOCUMENTS

| | | |
|---|---|---|
| EP | 0 396 387 A3 | 11/1990 |
| EP | 0396 387 A2 | 11/1990 |
| EP | 0 741 187 A2 | 11/1996 |
| EP | 0 956 862 A1 | 11/1999 |
| WO | WO 91/01004 | 1/1991 |
| WO | WO 94/11404 | 5/1994 |
| WO | WO 95/21864 | 8/1995 |
| WO | WO 96/05309 | 2/1996 |
| WO | WO 96/08510 | 3/1996 |
| WO | WO 96/23517 | 8/1996 |
| WO | WO 96/24670 | 8/1996 |
| WO | WO 96/31526 | 10/1996 |
| WO | WO 96/34885 A2 | 11/1996 |
| WO | WO 96/34885 A3 | 11/1996 |
| WO | WO 97/00319 | 1/1997 |
| WO | WO 97/12037 | 4/1997 |
| WO | WO 97/26335 | 7/1997 |
| WO | WO 97/48419 | 12/1997 |
| WO | WO 97/48806 | 12/1997 |
| WO | WO 98/28427 | 7/1998 |

OTHER PUBLICATIONS

Gura (Science vol. 286 pp 881–882), Oct. 29, 1999.*
Weigle et al (J. of Clin. Inv. vol. 96 Oct. 1995 pp 2065–2070).*
Bennett et al., "A role for leptin and its cognate receptor in hematopoiesis" *Curr. Biol.* 6:1170–1180 (1996).
Burguera et al., "The Long Form of the Leptin Receptor (OB–Rb) Is Widely Expressed in the Human Brain" *Neuriendocrin.* 71:187–195 (2000).
Hoggard et al., "Ontogeny of the expression of leptin and its receptor in the murine fetus and placenta" *Br. J. Nutr.* 83:317–326 (2000).
Luoh et al, "Cloning and characterization of a human leptin receptor using biologically active leptin ummunoadhesin" *J. Mo. Endocrin.* 18:77–85 (1997).

(List continued on next page.)

*Primary Examiner*—Mark Navarro
(74) *Attorney, Agent, or Firm*—Knobbe, Martens, Olson & Bear LLP.

(57) ABSTRACT

The present invention concerns long-half derivative of the obesity protein OB. The invention specifically concerns OB protein-immunoglobulin chimeras and polyethylene glycol (PEG)-OB derivatives, which have extended half-life as compared to the corresponding native OB proteins. The invention further relates to methods for treating obesity by using the long half-life derivatives of OB.

25 Claims, 27 Drawing Sheets

OTHER PUBLICATIONS

H. Baumann et al., "The full–length leptin receptor has signaling capabilities of interleukin 6–type cytokine receptors," *Proc. Natl. Acad. Sci. USA*, vol. 93, pp. 8374–8378 (Aug. 1996).

S. C. Chua Jr. et al., "Phenotypes of Mouse diabetes and Rat fatty Due to Mutations in the OB (Leptin) Receptor," *Science*, vol. 271, pp. 994–996 (Feb. 16, 1996).

G. E. Francis, *Focus on Growth Factors*, vol. 3, pp. 4–10 (1997).

Shin et al., *Hybrid Antibodies*, Intern. Rev. Immunol. vol. 10, pp. 177–186 (1993).

"Polyethylene glycol and derivatives" *Catalog Shearwater Polymers, Inc., Functionalized Biocompatible Polymers for Research* (Jan. 1994).

Ashkenazi and Chamow, "Immunoadhesins: An Alternative to Human Monoclonal Antibodies" *Methods: A Companion to Methods in Enzymology* 8:104–115 (1995).

Barin, Marcia, ""Obese" protein slims mice" *Science* 269:475–476 (1995).

Campfield et al., "Recombinant mouse ob protein: evidence for a peripheral signal linking adiposity and central neural networks" *Science* 269:546–549 (1995).

Cioffi et al., "Novel B219/OB receptor isoforms: possible role of leptin in hematopoiesis and reproduction" *Nature* 2(5):585–589 (1996).

Colditz, G.A., "Economic costs of obesity" *Am. J. Clin. Nutr.* 55:503S–507S (1992).

Coleman and Hummal, "Effects of parabiosis of normal with genetically diabetic mice" *Am. J. Physiol.* 217:1298–1304 (1969).

Coleman, D.L., "Effects of parabiosis of obese with diabetes and normal mice" *Diabetol* 9:294–298 (1973).

Considine, R. et al., "Serum immunoreactive–leptin concentrations in normal–weight and obese numans" *The New England Jornal of Medicine* pps. 292–295 (Feb. 1, 1996).

Friedman et al., "Molecular mapping of the mouse ob mutation" *Genomics* 11:1054–1062 (1991).

Halaas et al., "Weight–reducing effects of the plasma protein encoded by the obese gene" *Science* 269:543–546 (1995).

Kuczmarski et al., "Increasing prevalence of overweight among US adults" *J. Am. Med. Assoc.* 272(3):205–211 (1994).

Maffei et al., "Increased expression in adipocytes of ob RNA in mice with lesions of the hypothalamus and with mutations at the db locus" *Proc. Natl. Acad. Sci.* 92:6957–6960 (1995).

Pelleymounter et al., "Effects of the obese gene product on body weight regulation in ob/ob mice" *Science* 269:540–543 (1995).

Pi–Sunyer, F.X., "Medical Hazards of Obesity" *Anns. Int. Med.* 119:655–660 (1993).

Rink, Timothy J., "In search of a satiety factor" *Nature* 372:406–407 (1994).

Tartaglia et al., "Identification and expression cloning of a leptin receptor, ob–r" *Cell* 83:1263–1271 (1995).

Zhang et al., "Positional cloning of the mouse obese gene and its human homologue" *Nature* 372:425–431 (1994).

* cited by examiner

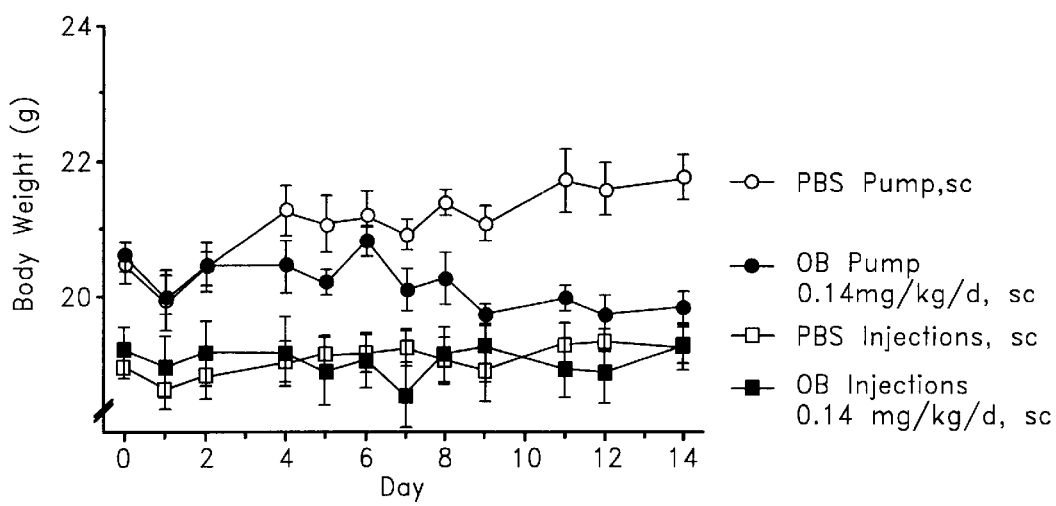
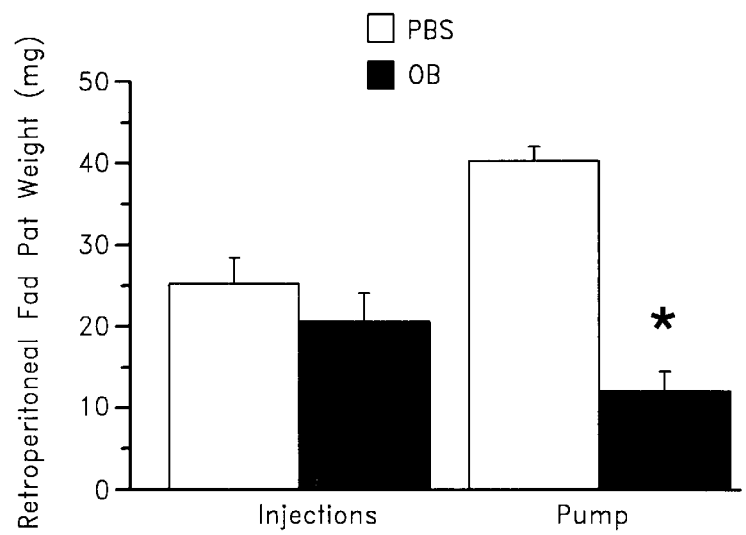
FIG. 1

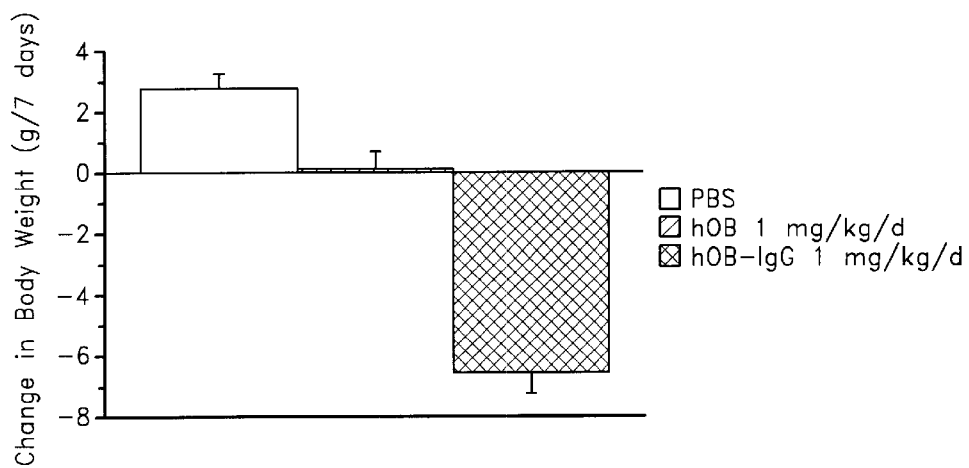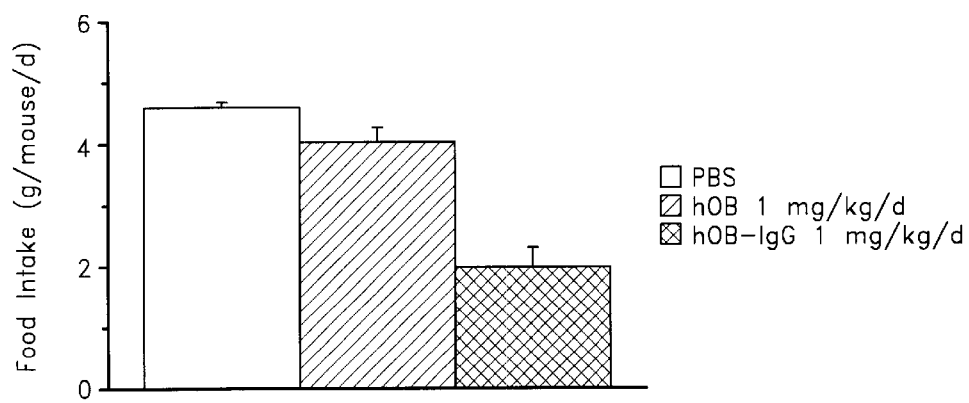
FIG. 3

PEG-hOB has Greater Activity than hOB
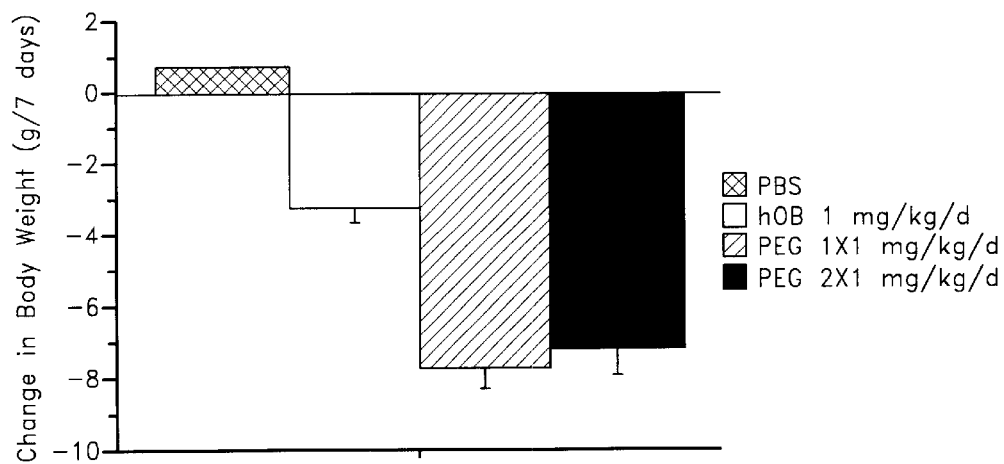
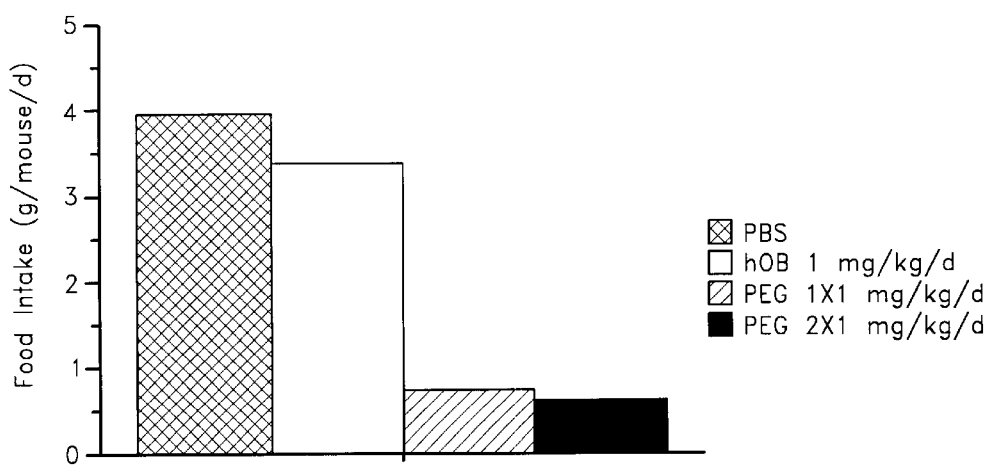
FIG. 4

FIG. 5A

```
> Tue Dec 19 09:59:19 1995
> /home/ruby/va/Molvio/sauvage/ob/ss.pRK5tkneo.hoBIgG
> sites: std
> length: 7127 (circular)
>assembled by Shiu-Ming Luoh Oct. 95
>human OB ClaI/BstEII cloning
>CMV enhancer/promoter thaI
                                                                                                    fnuDII/mvnI
                                                                                                    bstUI
                                                                                                    bsh1236I
      aluI                                                                              bslI        aciI maeIII
      sstI
      sacI
      hgiJII
      hgiAI/aspHI
      ecl136II
      bsp1286
      bsiHKAI
      bmyI          rmaI       tru9I
      banI          maeI       mseI
      taqI          speI       aseI/asnI/vspI
  1 TTCGAGCTCG CCCGACATTG ATTATTGACT AGTAATCAAT TACGGGGTCA TTAGTTCATA GCCCATATAT GGAGTTCCGC GTTACATAAC
    AAGCTCGAGC GGGCTGTAAC TAATAACTGA TCATTAGTTA ATGCCCCAGT AATCAAGTAT CGGGTATATA CCTCAAGGCG CAATGTATTG
                  scrFI
                  mvaI
                  ecoRII
                  dsaV
                  aciI
                  bglI bstNI                                    maeII
                  ssau96I                                       hinlI/acyI
                  haeIII/palI  aciI                             ahaII/bsaHI
                  asuI apyI9dcm+)                               aatII              maeII              maeIII
101 AATGCCATTT ACCGGGCGGA CCGACTGGCG GGTTGCTGGG GCCGGGTAAC TGCAGTTATT ACTGCATACA AGGGTATCAT TGCCGGTATC CCTGAAAGGT
    TTACGGTAAA TGGCCCGCCT GGCTGACCGC CCAACGACCC CGGCCCATTG ACGTCAATAA TGACGTATGT TCCCATAGTA ACGCCAATAG GGACTTTCCA
      maeII                                                                              maeII
      hinlI/acyI                                                                          hinlI/acyI
      ahaII/bsaHI                            bglI            rsaI                         ahaII/bsaHI
      aatII                                                  csp6I           ndeI         aatII          csp61
201 TTGACGTCAA TGGGTGGAGT ATTTACGGTA AACTGCCCAC TTGGCAGTAC ATCAAGTGTA TCATATGCCA AGTACGCCCC CTATTGACGT CAATGACGGT
    AACTGCAGTT ACCCACCTCA TAAATGCCAT TTGACGGGTG AACCGTCATG TAGTTCACAT AGTATACGGT TCATGCGGGG GATAACTGCA GTTACTGCCA
```

```
                                                                    nlaIII
     scrFI                                                 styI      ncoI
     mvaI                                                            dsaI hphI aciI
     ecoRII                                    rsaI     maeII        bsaJI     sfaNI
     aciI                                      csp6I    snaBI
     bglI dsaV                      rsaI                bsaAI
     sau96I bstNI                   csp6I
     haeIII/palI
     asuI apyI(dcm+)   bsrI nlaIII
301 AAATGGCCCG CCTGGCATTA TGCCCAGTAC ATGACCTTAT GGGACTTTCC TACTTGGCAG TACATCTACG TATTAGTCAT CGCTATTACC ATGGTGATGC
    TTTACCGGGC GGACCGTAAT ACGGGTCATG TACTGGAATA CCCTGAAAGG ATGAACCGTC ATGTAGATGC ATAATCAGTA GCGATAATGG TACCACTACG maeII
                                                                  hinlI/acyI                            nlaIV
             rsaI                                                 ahaII/bsaHI                           hgiCI
             csp6I                                 bsmAI          aatII                                 banI
401 GGTTTTGGCA GTACATCAAT GGGCGTGGAT AGCGGTTTGA CTCACGGGGA TTTCCAAGTC TCCACCCCAT TGACGTCAAT GGGAGTTTGT TTTGGCACCA
    CCAAAACCGT CATGTAGTTA CCCGCACCTA TCGCCAAACT GAGTGCCCCT AAAGGTTCAG AGGTGGGGTA ACTGCAGTTA CCCTCAAACA AAACCGTGGT aluI
                                                                                                           sstI
                                                                                                           sacI
                       pleI                                                                                hgiJII
                aciI   hinfI                                                                               hgiAI/aspHI
                                                                                                           ecl136II
                                                                                                           bsp1286
                                                                                                           bsiHKAI
                                           maeIII                                                          bmyI
                                           aciI      hgaI        aciI           rsaI                       banII
                                                                                csp6I     mnlI
501 AAATCAACGG GACTTTCCAA AATGTCGTAA CAACTCCGCC CCATTGACGC AAATGGGCGG TAGGCGTGTA CGGTGGGAGG TCTATATAAG CAGAGCTCGT
    TTTAGTTGCC CTGAAAGGTT TTACAGCATT GTTGAGGCGG GGTAACTGCG TTTACCCGCC ATCCGCACAT GCCACCCTCC AGATATATTC GTCTCGAGCA
```

```
                                                                          sau96I
                                                                          avaII
                                                                          asuI
                                                                          scrFI
                                                                          mvaI
                                                                          ecoRII
                                                                          dsaV
                                                                          bstNI
                                          maeIII                          apyI[dcm+]
                                          hphI    scfI    fokI            bslI bsaJI
801 CATAACCTTA TGTATCATAC ACATACGATT TAGGTGACAC TATAGAATAA CATCCACTTT GCCTTTCTCT CCACAGGTGT CCACTCCCAG GTCCAACTGC
    GTATTGGGAAT ACATAGTATG TGTATGCTAA ATCCACTGTG ATATCTTATT GTAGGTGAAA CGGAAAGAGA GGTGTCCACA GGTGAGGGTC CAGGTTGACG
                                                         ^sp6 RNA start mnlI        ppu10I                         tfiI        sau96I
    bsaJI       taqI nsiI/avaIII               hinfI       haeIII/palI
                claI/bsp106      nlaIV    aciI             asuI                            bsp1286
901 ACCTCGGTTC TATCGATATG CATTGGGGAA CCCTGTGCGG ATTCCTGTGG CTTTGGCCCT ATCTTTTCTA TGTCCAAGCT GTGCCCATCC AAAAAGTCCA
    TGGAGCCAAG ATAGCTATAC GTAACCCCTT GGGACACGCC TAAGAACACC GAAACCGGGA TAGAAAAGAT ACAGGTTCGA CACGGGTAGG TTTTTCAGT
                                                                                  aluI bmyI fokI
  1                                         Met HisTrpGlyT hrLeuCysGl yPheLeuTrp yrLeuPheTy rValGlnAla ValProIleG lnLysValGln
        ^cloning linker  ^human OB start sau3AI
                    mboI/ndeII[dam-]
                    dpnI[dam+]
                    scrFI
                    mvaI
                    ecoRII
                    dsaV                                                                         mspI
                    stNI                                                                   hpaII
                    apyI[dcm+]                                                              cfr10I
                    hphI  dpnII[dam-]                                            bsmAI             bsaWI
         mnlI       maeIII alwI[dam-]                                            mnlI              ageI
         mnlI       munI                                                                           hphI
1001 AGATGACACC AAAACCCTCA TCAAGACAAT TGTCACCAGG ATCAATGACA TTTCACACAC GCAGTCAGTC TCCTCCAAAC AGAAAGTCAC CGGTTTGGAC
     TCTACTGTGG TTTTGGGAGT AGTTCTGTTA ACAGTGGTCC TAGTTACTGT AAAGTGTGTG CGTCAGTCAG AGGAGGTTTG TCTTTCAGTG GCCAAACCTG
  29 AspAspThr LysThrLeuI leLysThrIl eValThrArg IleAsnAspI leSerHisTh rGlnSerVal SerSerLysG lnLysValTh rGlyLeuAsp
```

```
                                                                                                                                              scrFI
                                                                                                                                              mvaI
                                                                                                                                              ecoRII
                                                                                                                                              dsaV
                                                                                                              scrFI                           bstNI
                                                                                                              mvaI                   ecoNI    apyI[dcm+]
                                                                                                              ecoRII        hphI     bsII     cctgcaccag
                                                                                         rsaI                 dsaV  hgaI    mnlI     cctcaccgt ggactggtc
                                                                                         csp6I                maeII gtggtcagcg tcctcaccgt ggagtggca lleuhisgln
                                    aciI                                                 bsaI                 cacgtaccgt gtgcatggca agagtcgc ileuhisgln
                                    thaI                                                 agtacaacag          cacgtaccgt gtgcatggca ggagtggca
                                    fnuDII/mvnI                                          tcatgttgtc          gtgcatggca
                                    bstUI                                                lnTyrAsnSe          rThrTyrArg ValValSerV aLeuThrVa
                                    bshl236I
                                    sacII/sstII                                                                                         fnu4HI
                                    nspBII                                        rsaI                                                 bbvI  avaI
                                    kspI                                          csp6I      mnlI               tagI                   cagccccgag
                                    dsaI                             bsmaAI       cccagccccc   atcgagaaaa ccatctccaa agccaaaggg cagcccgag
                          mnlI      bsaJI       fnu4HI    mnlI       aaggtctcca    acaaagcct   tagctcttt  ggtagaggtt tcggtttccc gtcgggctc
                          ataatgccaa ga****gccg cgggaggagc gcccctctg gccc          tgttcggga gggtcggggg uproalapro hrileSerLy sAlaLysGly GlnProArgGlu
1601 cgtggacggc gtggaggtgc ataatgccaa gccc*gccg cgggaggagc gcccctctg ggtctctg ccc cagccccc
     gcacctgccg cacctccacg tattacggtt ctgtttcggc gccccctccg                       tgttcggga    cccagccccc  atcgagaaaa ccatctccaa agccaaaggg cagcccgag
229  ValAspGly ValGluValH isAsnAlaLy sThrLysPro ArgGluGluG lnTyrAsnSe rThrTyrArg ValValSerV aLeuThrVa lLeuHisGln bsrI         rsaI       bsmaAI
                        csp6I      bsaI           mnlI
1701 gactggctga atggcaagga gtacaagtgc aaggtctcca acaaagcccc cccagccccc atcgagaaaa ccatctccaa agccaaaggg cagccccgag
     ctgaccgact taccgttcct catgttcacg ttccagaggt tgtttcggga gggtcgggg tagctcttt ggtagaggtt tcggtttccc gtcgggctc
262  AspTrpLeuA snGlyLysGl uTyrLysCys LysValSerA snLysAlaLe uProAlaPro hrIleSerLy sAlaLysGly GlnProArgGlu scrFI
                                           ncil
                                           mspI
                                           hpaII
                                           dsaV
                                           cauII
                                           xmaI/pspAI
                                           smaI
                                           scrFI                              scrFI
                                           ncil                               mvaI
                                           dsaV                               ecoRII                           bstNI
                                           cauII                              dsaV                             apyI[dcm+]       bstNI         dsaI
                        rsaI                                                  bstNI                            bspMI            apyI[dcm+]    bsII
                        csp6I    fokI                                         apyI[dcm+]                                                      bsaJI
     bspl407I           bsII bsaJI avaI  earI/ksp632I                         sexAI
1801 aaccacagt gtacaccctg cccccatccc gggaagagat gaccaagaac caggtcagcc tgacctgcct ggtcaaaggc ttctatccca gggacatgcg
     ttggtgtcca catgtgggac gggggtaggg ccctctct ctggttcttg gtccagtcgg actgggacgga ccagttccg aagataggg cgctgtaggcg
296  ProGlnVa  lTyrThrLeu ProProSerA rgGluGluMe tThrLysAsn GlnValSerL euThrCysLe uValLysGly PheTyrProS erAspIleAla
```

FIG. 5H

```
                                    mspI
                                    hpaII
                                    fnu4HI
                                    bbvI                                                                                                                    dsaI
                                                                                                     pleI                         mnlI                      hphI
                                                            mnlI                                     hinfI     nlaIV mboII       scfI                       aluI bsaJI
1901 CGTGGAGTGG GAGAGCAATG GGCAGCCGGA GAACAACTAC AAGACCACGC CTCCCGTGCT GGACTCCGAC GGCTCCTTCT TCCTCTACAG CAAGCTCACC
     GCACCTCACC CTCTCGTTAC CCGTCGGCCT CTTGTTGATG TTCTGGTGCG GAGGGCACGA CCTGAGGCTG CCGAGGAAGA AGGAGATGTC GTTCGAGTGG
 329 ValGluTrp GluSerAsnG lyGlnProGl uAsnAsnTyr LysThrThrP roProValLe uAspSerAsp GlySerPheP heLeuTyrSe rLysLeuThr scrFi
                                                                                                                                                             nciI
                                                             m***                                                                                            mspI
                                                             bpu**                      nlaIII                                                               hpaII
                                                             maeII                      ppulOI                                          sapI                 dsaV
                                   fnu4HI     xmnI bbsI              nlaIII     nsiI/avaIII                                             mboII mnlI    bsmAI
                        bspMI bbvI asp700                            sfaNI      mnlI                                            earI/ksp632I bslI     cauII
2001 GTGGACAAGA GCAGGTGGCA GCAGGGAAAC GTCTTCTCAT GCTCCGTGAT GCATGAGGCT CTGCACAACC ACTACACGCA GAAGAGCCTG TCCCTGTCTC
     CACCTGTTCT CGTCCACCGT CGTCCCCTTG CAGAAGAGTA CGAGGCACTA CGTACTCCGA GACGTGTTGG TGATGTGCGT CTTCTCGGAG AGGGACAGAG
 362 ValAspLysS erArgTrpGl nGlyGlyAsn ValPheSerC ysSerValMe tHisGluAla LeuHisAsnH isTyrThrGl nLysSerLeu SerLeuSerPro sau96I
                                                                                                  nlaIII
                                                                                         fnu4HI   haeIII/palI
                                                                                         bglI styI
                                                                  taqI            scfI   sfiI ncoI
                                                                  salI            pstI   eaeI dsaI
                                                             pleI        rmaI salI hincII/hindII     cfrI bsaJI                                               aluI
                                                    sau96I hinfI         xbaI maeI accI bsgI             aluI haeIII/palI                                     fnu4HI
                                                    haeIII/palI  pstI                                    hindIII aciI asuI                                    bbvI
                                          asuI maeI accI bspMI   bsgI    aluI maeI hinfI bspMI           hindIII
2101 CGGGTAAATG AGTGCGACGG CCCTAGAGTC GACCTGCAGA AGCTTCTAGA GTCGACCTGC AGAAGCTTGG CCGCCATGGC CCAACTTGTT TATTGCAGCT
     GCCCATTTAC TCACGCTGCC GGGATCTCAG CTGGACGTCT TCGAAGATCT CAGCTGGACG TCTTCGAACC GGCGGTACCG GGTTGAACAA ATAACGTCGA
 396 GlyLys ^sv40 early poly A
```

```
                                                                              fnu4HI
                                                                              bglI
                                                                              sfiI
                                                                              haeIII/palI
                                                           nlaIII              mnlI  mnlI    ddeI
                                                           styI                haeIII/palI bsaJI mnlI  aluI
                                                           ncoI                mnlI bsaJI aciI    haeIII/palI
                          bsrI           bslI dsaI
        aciI                     aciI bsaJI                  mnlI bsaJI aciI    haeIII/palI                         scrFI
aciI                                                                                                                mvaI
2601 CGCCCCCTAA CTCCGCCCAG TTCCGCCCCAT TCTCCGCCCC ATGGCTGACT AATTTTTTTT ATTTATGCAG AGGCCGAGGC CGCCTCGGCC TCTGAGCTAT
     GGCGGGGATT GAGGCGGGTC AAGGCGGGGTA AGAGGCGGGG TACCGACTGA TTAAAAAAAA TAAATACGTC TCCGGCTCCG GCGGAGCCGG AGACTCGATA
                                                                                                                    sau96I
                                                                                                                    nlaIV
                                                                                                                    avaII   sau96I
                                                                                                                    thaI    ecoRII
                                                                                                                    fnuDII/mvnI
                                                                                                                    bstUI  dsaV
                                                  sfuI                                                              bsh1236I  avaII
                                                  bstBI                                                             hinPI   bstNI
                            styI                  bsiCI                                                             hhaI/cfoI  asuI
                            bsaJI                 asuII                                                             fnu4HI asuI apyI[dcm+]
                            blnI                  tru9I                                                             aciI aciI bsaJI
               mnlI         haeIII/palI           aluI mseI taqI               sfaNI                                sau3AI
               mnlI         stuI rmaI                                                                               mboI/ndeII[dam-]
               mnlI         haeI maeI                                                                               dpnI[dam+]
                            mnlI avrII
2701 TCCAGAAGTA GTGAGGAGGC TTTTTTGGAG GCCTAGGCTT TTGCAAAAAG CTGTTAATTC GAACACGCAG ATGCAGTCGG GGCGGGCGGG TCCCAGGTCC
     AGGTCTTCAT CACTCCTCCG AAAAAACCTC CGGATCCGAA AACGTTTTTC GACAATTAAG CTTGTGCGTC TACGTCAGCC CCGCCCGCCC AGGGTCCAGG
                                                                                       ^start pUC118
                                                                                 ^TK promoter                       sau3AI
                                                                                                                    mboI/ndeII[dam-]
                                                                                                                    dpnI[dam+]
                                                       fnu4HI                                                       bstYI/xhoII
                                                       bbvI                                                         bglII dpnII[dam-]
                       thaI                            scfI                                                         fnu4HI bclI[dam-] bsmAI
                       fnuDII/mvnI                     pstI                       tru9I hincII/hindII aciI dpnII[dam-] bsmAI
                       bstUI                           bsgI          aciI mseI hgaI                                 
                       mluI          haeIII/palI              aciI mseI hgaI
                       afIIII
          hphI bsh1236I  mnlI
      tru9I hgaI         haeI taqI
      mseI maeIII
2801 ACTTCGCATA TTAAGGTGAC GGTGTGGCC TC***CACCG AGCGACCCTG CAGGCGACCCG CTTAACAGCG TCAACAGCGT GCCGCAGATC TGATCAAGAG
     TGAAGCGTAT AATTCCACTG CCACACCGG AG***GTGGC TCGCTGGGAC GTCCGCTGGGC GAATTGTCGC AGTTGTCGCA CGGCGTCTAG ACTAGTTCTC
                                                            tn5 neomycin phosphotransferase gene.
```

FIG. 5K

```
              scrFI
              nciI       sau3AI
              mspI       mboI/ndeII[****]
              hpaII      dpnI[dam+]
              dsaV       dpnII[dam-]
              cauII      bstYI/xhoI
              bsaJI      alwI[dam-]                                                                    hphI                                    fnu4HI
                                                                                           nlaIII sfaNI                                        fnu4HI
                                                                                                                                               aciI
                                                                                                                                               fnu4HI      aciI bbvI
3201 TTGGGCGAAG TGCCGGGGCA GGATCTCCTG TCATCTCACC TTGCTCCTGC CGAGAAAGTA TCCATCATGG CTGATGCAAT GCGGCGGCTG
     AACCCGCTTC ACGGCCCCGT CCTAGAGGAC AGTAGAGTGG AACGAGGACG GCTCTTTCAT AGGTAGTACC GACTACGTTA CGCCGCCGAC sau3AI
                                                                                                                    mboI/ndeII[dam-]
                                                                                                                    dpnI[dam+]
                                                                                                                    dpnII[dam-]
                                                                                                                    alwI[dam-]
                                                                                                        CATACGCTTG
                                                                                                        GTATGCGAAC rsaI
                                                          csp6I
                                                          bsaAI                                                         sau3AI
                                                          hgiAI/aspHI                                                   mboI/ndeII[dam]
                                                          bsp1286                                                       fokI
                                              taqI        bsiHKAI                                               mspI    sau3AI      dpnI[dam+]      sapI
      mspI                                    sfaNI       bmyI maeII        fokI                                hpaII   mboI/ndeII[dam+]            mboII
      hpaII bspMI      taqI                                                                                     cfr10I  dpnI[dam-]                  earI/ksp632I
                                                                                                                        taqI[dam-] dpnII[dam-]
3301 ATCCGGCTAC CTGCCCATTC GACCACCAAG CGAAACATCG CATCGAGCGA GCACGTACTG GGATGGAAGC CGGTCTTGTC GATCAGGATG ATCTGGACGA
     TAGGCCGATG GACGGGTAAG CTGGTGGTTC GCTTTGTAGC GTAGCTCGCT CGTGCATGAC CCTACCTTCG GCCAGAACAG CTAGTCCTAC TAGACCTGCT
```

```
                                          sphI
                                          nspI
                                          nspHI
                                          hinPI
                                          hhaI/cfoI
                                          thaI               sau3AI
             hinPI                                           mboI/ndeII[dam-]
             thaI                                            dpnII[dam+]       styI
             fnuDII/mvnI            scrFI  fnuDII/mvnI       bstYI/xhoII       ncoI
             bstUI                  mval   bstUI             dpnII[dam-]       dsaI
          hgiJII                    ecoRII bsh1236I          alwI[dam-]
          bsp1286                   dsaV   hinPI  nlaIII     mnlI              bsaJI   sfaNI
          bmyI bsh1236I             bstNI  hhaI/cfoI                           maeIII  nlaIII
       sfaNI banII hhaI/cfoI        apyI[dcm+] gssHII
3401 AGAGCATCAG GGGCTCGCGC CAGCCGAACT GTTCGGCGGC CTCAAGGCGC GCATGCCCGA CGGCGAGGAT CTCGTCGTGA CCCATGGCGA TGCCTGCTTG
     TCTCGTAGTC CCCGAGCGCG GTCGGCTTGA CAAGCCGCCG GAGTTCCGCG CGTACGGGCT GCCGCTCCTA GAGCAGCACT GGGTACCGCT ACGGACGAAC
                                                                    mspI           bslI
                                                                    hpaII          sau96I
                                                                    naeI           avaII
                                    aciI                            cfr10I         asuI
                                    fnu4HI                          haeIII/palI    rsrII/cspI
                                    haeIII/palI                     eaeI           cpoI
                                    eaeI         tfiI               cfrI           aciI aciI
             nlaIII                 cfrI         hinfI  taqI
3501 CCGAATATCA TGGTGGAAAA TGGCCGCTTT TCTGGATTCA TCGACTGTGG CCGGCTGGGT GTGGCGGACC GCTATCAGGA CATAGCGTTG GCTACCCGTG
     GGCTTATAGT ACCACCTTTT ACCGGCGAAA AGACCTAAGT AGCTGACACC GGCCGACCCA CACCGCCTGG CGATAGTCCT GTATCGCAAC CGATGGGCAC
                                                                                              hinPI
             sapI                                                              bsrBI          hhaI/cfoI
             mboII    fnu4HI                                                   aciI  tfiI    fnu4HI
             earI/ksp632I                        ciI    mnlI                   fnu4HI hinfI  bbvI sfaNI
             eco57I aluI aciI
3601 ATATTGCTGA AGAGCTTGGC GGGCAATGGG CCGCTTACCC CT))CGCTT CCTCGTGCTT TACGGTATCG CCGCTCCCGA TTCGCAGCGC ATCGCCTTCT ATCGCCTTCT
     TATAACGACT TCTCGAACCG CCCGTTACCC GGCGAATGGG    )GCGAA GGAGCACGAA ATGCCATAGC GGCGAGGGCT AAGCGTCGCG TAGCGGAAGA TAGCGGAAGA
                                   taqI
                                   sfuI
                                   bstBI    hinII/acyI
                            aciI   bsiCI    hgaI  gspMI                              tfiI   aciI
                  ddeI  pleI       asuII    asaII/bsaHI                              hinfI  fnu4HI
           mboII  bsrBI hinfI                                                        taqI   aciI
3701 TGACGAGTTC TTCTGAGCGG GACTCTGGGG TTCGAAATGA CCGACCAAGC GACGCCCAAC CTGCCATCAC GAGATTTCGA TTCCACCGCC GCCTTCTATG
     ACTGCTCAAG AAGACTCGCC CTGAGACCCC AAGCTTTACT GGCTGGTTCG CTGCGGGTTG GACGGTAGTG CTCTAAAGCT AAGGTGGCGG CGGAAGATAC
```

FIG. 5N

```
                                                          scrFI
                                                          nciI
                                                          mspI
                                                          hpaII
                                                          dsaV
                                                          cauII
                                                          bslI
                                                          xmaI/pspAI
                                                          smaI
                                                          scrFI
                                                          nciI
                                                          dsaV
                               hinII/acyI   thaI  sau3AI  cauII
                               hgaI     bslI fnuDII/mvnI  bsaJI
                               ahaII/bsaHI  gsuI/bpmI bstYI/xhoII  bsaJI
                     scrFI             mnlI hinPI alwI[dam-]       mboII bslI avaI
                     nciI        sau3AI hhaI/cfoI      qsuI/bpmI
                     mspI    mboI/ndeII[dam-] mboI/ndeII[dam-]
                     hpaII     dpnI[dam+] bstUI dpnI[dam-]
              tfiI   naeI     dpnII[dam-] aciI dpnII[dam-]
              hinfI  dsaV  cfrIOI fokI alwI[dam-] bsh1236U   nlaIII       mboII
              cauII
3801 AAAGGTTGGG CTTCGGAATC GTTTTCCGGG ACGCCGGCTG GATGATCCTC CAGCGCGGGG ATCTCATGCT GGAGTTCTTC GCCCACCCCG GGAGATGGGG
     TTTCCAACCC GAAGCCTTAG CAAAAGGCCC TGCGGCCGAC CTACTAGGAG GTCGCGCCCC TAGAGTACGA CCTCAAGAAG CGGGTGGGGC CCTCTACCCC
                                                                                 HSV1 tk terminator SmaI-PvuII  ^ hinPI
                                  hhaI/cfoI
                                  thaI
                                  fnuDII/mvnI
                                  bstUI
                                  bsh1236I
                          mspI
                          hpaII
            mnlI          bsaWI  nlaIV aciI
3901 GAGGCTAACT GAAACACGGA AGGAGACAAT ACC*GAAGGA ACCCGCGCTA TGACGGCAAT AAAAAGACAG TTTTCTGTC TTATTTTGCG TGCCCACAAC ACGGGTGTTG GGTCGTTTGT
     CTCCGATTGA CTTTGTGCCT TCCTCTGTTA TGG****TCCT TGGGCGCGAT ACTGCCGTTA TTTTTCTGTC TAAAAGACAG AATAAAACGC ACGGGTGTTG GGTCGTTTGT CCAGCAAACA
            scrFI
            mvaI
            ecoRII
            dsav
            bstNI
            bsaJI
            bslI
     aciI  sau96I
     thaI  nlaIV                                                               thaI
     fnuDII/mvnI bsaJI                                      haeIII/palI        fnuDII/mvnI
     bstUI   avaII                                          sau96I              bstUI
     bsh1236I asuI apyI[dcm+]                         bsmAI asuI                bsh1236I
            taqI                                      bsaI  nlaIV               aciI     mboII
4001 TCATAAACGC GGGGTTCGGT CCCAGGGCTG GCACTCTGTC GATACCCCAC CGAGACCCCA TTGGGCCCAA TACGCCCGCG AACCCGGTT ATGCGGGCGC TTTCTTCCTT TTCCCCACCC
     AGTATTTGCG CCCCAAGCCA GGGTCCCGAC CGTGAGACAG CTATGGGGTG GCTCTGGGGT AACCCGGGTT ATGCGGGCGC TTGGGCCAA TAGCGCCCGC AAAGAAGGAA AAGGGGTGGG
```

FIG. 50

```
                                                                                    aciI
                                                                                    thaI
                                                                                    fnuDII/mvnI
                                                                                    bstUI
                                                                                    sacII/sstII
                                                                      haeIII/palI bsh1236I
                                                                      mcrI        nspBII
                                                                         dsaI    kspI
                                                                         bsaJI   dsaI
                                                              mnII hinPI    hphI eagI/xmaIII/eclXI
                                                              rsaI hhaI/cfoI    eaeI        bsaJI
                                               mboII          csp6I eco47III    maeIII      aciI
           mspI                                                                 bstEII   cfrI
           hpaII            bslI       sfaNI
         aciI
         fnu4HI GCCGCCGGAC GAACTAAACC TGACTACGGC ATCCTCTGCCC CTTCTTCGCT GGTACGAGGA GCGCTTTTGT TTTGTATTGG TCACCACGGC CGAGTTTCCG
    4401 CGGCGGCCTG CTTGATTTGG ACTGATGCCG TAGAGACGGG GAAGAAGCGA CCATGCTCCT CGCGAAAACA AAACATAACC AGTGGTGCCG GCTCAAAGGC scrFI       nlaIV
         nciI        hgiCI
         dsaV        scrFI
         cauII       mvaI
         bslI        ecoRII
         bslI        dsaV
         bsaJI       bstNI
         sau961      bsaJI
         nlaIV       haeIII/palI
         avaII       eaeI                                                                        hinPI      mspI
         asuI  cfrI  bsp1286                                                                     hhaI/cfoI  bsII
         ppuMI mspI  apyI[dcm+]                                    mboII                         hpaII
         nlaIV hpaII bmyI                                          bpuAI                   thaI  fnuDII/mvnI
         eco0109I/draII banI                    nlaIII             bbsI    aciI  bcgI            bstUI bsaWI
                                                                                  nlaIII aciI bslI bsh1236I        aluI
    4501 CGGGACCCCG GCCAGGGCAC CTGTCCTACG AGTTGCATGA TAAAGAAGAC AGTCATAAGT GCGGCGACGA TAGTCATGCC CCGCGCCCAC CGGAAGGAGC
         GCCCTGGGGC CGGTCCCGTG GACAGGATGC TCAACGTACT ATTTCTTCTG TCAGTATTCA CGCCGCTGCT ATCAGTACGG GGCGCGGGTG GCCTTCCTCG
             ^pBR322 sequence
```

FIG. 5P

```
                                                      fnu4HI
                                                      haeIII/palI
                                                      mcrI
                                                      eagI/xmaIII/eclxI
                                                      eaeI                               hinPI                       aciI
                                                      notI                               thaI                        fnu4HI
                                                      fnu4HI                             fnuDII/mvnI                 thaI
                                                      aciI                               bstUI   scfI     hinPI      fnuDII/mvnI
                                    mcrI  bsrBI aciI                           rsaI hhaI/cfoI  bsh1236I  hhaI/cfoI   bstUI
                                    sfaNI taqI cfrI sfaNI                      csptI bslI      fnu4HI    tru9I aciI  hinPI
    bsrI                                                                                        aciI      msel bsh1236I     hhaI/cfoI
4601 TGACTGGGTT GAAGGCTCTC AAGGGCATCG GTCGAGCGGC CAACCATAAAG CAACCATAAAG ACGCGCCCTG TAGCGGCGCA TTAAGCCGGG CGGGTGTGGT
     ACTGACCCAA CTTCCGAGAG TTCCCGTAGC CAGCTCGCCG GTTGGTATCA GTTGGTATCA TGCGCGGGAC ATCGCCGCGT AATTCGGCCC GCCCAGACCA
                                                                    ^delta 3
                                                                    ^M13 ori fnu4HI
         hinPI
         hhaI/cfoI                                  hinPI                                                         mspI
         thaI                                       hhaI/cfoI                                                     hpaII
         fnuDII/mvnI                 rmaI                                                                         naeI
         bstUI                       hinPI  haeI                                                              maeII cfr10I
         bsh1236I          aciI      hhaI/cfoI  maeI  aciI                                       mboII
     maeIII bbvI maeIII              haeIII maeI            aciI
4701 GGTTACGCGC AGCGTGACCG CTACACTTGC GCGCCCGCTC CTTCCCCTTCC TTTCTCGCCA CGTTCGCCGG CTTTCCCCGT
     CCAATGCGCG TCGCACTGGC GATGTGAACG CGCGGGCGAT CGCGGGGCGAG GAAAGCGAAA GAAGGAAGG AAAGAGCGGT GCAAGCGGCT GAAAGGGGCA nlaIV
                    hgiJII
                    bsp1286                              nlaIV                                                maeII haeIII/palI
                    bmyI                                 hgiCI  taqI                                          draIII sau96I
                    banII              nlaIV             banI   mnlI                            hphI          bsaAI  asuI
          aluI              nlaIV
4801 CAAGCTCTAA ATCGGGGGCT CCCTTTAGGG TTCCGATTTA GTGCTTTACG GCACCTCGAC CCCAAAAAAC TTGATTTGGG TGATGGTTCA CGTAGTGGGC
     GTTCGAGATT TAGCCCCCGA GGGAAATCCC AAGGCTAAAT CACGAAATGC CGTGGAGCTG GGGTTTTTTG AACTAAACCC ACTACCAAGT GCATCACCCG
```

```
                                              hgiAI/aspHI
                                              bsp1286
                                              bsiHKAI                    sau3AI
                      sau3AI                                              bmoI/ndeII[dam-]         sau3AI
                      mboI/ndeII[dam-]                                    dpnI[dam+]               mboI/ndeII[dam-]
                      dpnI[dam+]    bmyI                                  dpnII[dam-]              dpnI[dam+]
                      dpnII[dam-]   apaLI/snoI                            bstYI/xhoI               dpnII[dam-]
              eco57I                alw44I/snoI   maeIII  taqI  alwI[dam-]  bsrI      nspBII       alwI[dam-]
      hphI    sfaNI   mboII[dam-]                                                    aciI          bstYI/xhoII          mboII
5401  GGTGAAAGTA AAAGATCTG AAGATCAGTT GGGTGCACCA GTGGGTTACA TCGAACTGGA TCTCAACAGC GGTAAGATCC TTGAGAGTTT TCGCCCCGAA
      CCACTTTCAT TTTCTACGAC TTCTAGTCAA CCCACGTGGT CACCCAATGT AGCTTGACCT AGAGTTGTCG CCATTCTAGG AACTCTCAAA AGCGGGGCTT scrFI
                                                                                   nciI
                                                                                   mspI
                                                             aciI                  hpaII
                                                             thaI                  dsaV
                                                             fnuDII/mvnI           cauII
                                                             bstUI                 hinII/acyI
              maeII                                          bsh1236I              hgaI                 aciI
              psp1406I                                       hinPI                 ahaII/bsaHI  bcgI    mcrI  fnu4HI
      xcmI                                           ahaII/draI  hhaI/cfoI         ATTATCCCGT GATGACGCCG GGCAAGAGCA ACTCGGTCGC CGCATACACT
      asp700  bmyI                   GTTCTGCTAT GTGGCGCGGT CAAGACGATA CACCGCGCCA TAATAGGGCA CTACTGCGGC CCGTTCTCGT TGAGCCAGCG GCGTATGTGA
5501  GAACGTTTC CAATGATGAG CACTTTTAAA
      CTTGCAAAAG GTTACTACTC GTGAAAATTT rsaI
              csp6I  bsrI
              scaI   hphI   maeIII                       sfaNI   foki  nlaIII                                        fnu4HI
      ddeI                                                                                                           bbvI    nlaIII
5601  ATTCTCAGAA TGACTTGGTT GACTACTCAC CAGTGACTCA AAAGCATCTT ACGGATGGCA TGACAGTAAG AGAATTATGC AGTGCTGCCA TAACCATGAG
      TAAGAGTCTT ACTGAACCAA CTGATGAGTG GTCAGTGAGT TTTCGTAGAA TGCCTACCGT ACTGTCATTC TCTTAATACG TCACGACGGT ATTGGTACTC
```

```
                                                              sau96I
                                                              avaII
                                   sau3AI                     asuI
                                   mboI/ndeII[dam-]
                                   dpnI[dam+]
              haeIII/palI          dpnII[dam-]
              eaeI                 pvuII/bspCI
              cfrI                 mcrI mnlI                                                    nlaIII
              fnu4HI                                                                            sau3AI maeIII
              aciI                                   aluI aciI       nlaIII dpnII[dam-]         mboI/ndeII[dam-]
                                                                                                dpnI[dam+]
                                                                                                alwI[dam-]
5701 TGATAACACT GCGGCCAACT TACTTCTGAC AACGATCGGA GGACCGAAGG AGCTAACCGC TTTTTTGCAC AACATGGGGG ATCATGTAAC
     ACTATTGTGA CGCCGGTTGA ATGAAGACTG TTGCTAGCCT CCTGGCTTCC TCGATTGGCG AAAAAACGTG TTGTACCCCC TAGTACATTG sau3AI
                                                                                              mboI/ndeII[dam-]
                                                                                              dpnI[dam+]
                                                                                              dpnII[dam-]
                                                                                              TCGCCTTGAT
                                                                                              ACCGGAACTA hinPI
                                                                                     mstI
         mspI                                                                        aviII/fspI      bsrI
         hpaII                                                           fnu4HI      maeII hhaI/cfoI tru9I
         bsaWI                                                           bbvI        psp1406I        mseI
     nlaIV     aluI                                maeIII       sfaNI
5801 CGTTGGGAAC CGGAGCTGAA TGAAGCCATA CCAAACGACG AGCGTGACAC CACGATGCCA CAACAACGTT GCGCAAACTA TTAACTGGCG
     GCAACCCTTG GCCTCGACTT ACTTCGGTAT GGTTTGCTGC TCGCACTGTG GTGCTACGGT GTTGTTGCAA CGCGTTTGAT AATTGACCGC mspI
              hpaII
              scrFI                                                           bhlI
          aluI ncII     tru9I      fokI                                       sau96I
          alu  ncII     mseI       bsrI           aciI                        haeIII/palI
          rmaI dsaV                asnI/vspI      msII                        asuI         hinPI  mspI
          maeI cauII     aseI/     bsrI                                       hhaI/cfoI    hpaII
                                                                                           asuI
5901 AACTACTTAC TCTAGCTTCC CGGCAACAAT TAATAGACTG GATGGAGGCC GATAAAGTTG CAGGACCACT TCTGCGCTCG GCCCTTCCGG CTGGCTGGTT
     TTGATGAATG AGATCGAAGG GCCGTTGTTA ATTATCTGAC CTACCTCCGG CTATTTCAAC GTCCTGGTGA AGACGCGAGC CGGGAAGGCC GACCGACCAA
```

```
                                                            acuU
                                                            thaI
                                             mspI           fnuDII/mvnI        sau96I
                                             hpaII          bstUI              asuI                                                 eam1105I
                                             cfr10I                            nlaIV
                     nlaIV hphI              bsmAI          fnu4HI
           gsuI/bpmI                   bsaI bsh1236I        bbvI bsrI haeIII/palI     mnlI
6001 TATTGCTGAT AAATCTGGAG CCGGTGAGCG TGGGTCTCGC GGTATCATTG CAGCACTGGG GCCAGATGGT AAGCCCTCCC GTATCGTAGT TATCTACACG
     ATAACGACTA TTTAGACCTC GGCCACTCGC ACCCAGAGCG CCATAGTAAC GTCGTGACCC CGGTCTACCA TTCGGGAGGG CATAGCATCA ATAGATGTGC ddeI
                                           sau3AI         nlaIV
                                           mboI/ndeII[dam-]  mnlI
                              pleI         dpnI[dam+]    hgiCI       tru9I
                              hinfI        dpnII[dam=]   banI        mseI             maeIII
                                   fokI
6601 ACGGGGAGTC AGGCAACTAT GGATGAACGA AATAGACAGA TCGCTGAGAT AGGTGCCTCA CTGATTAAGC ATTGGTAACT GTCAGACCAA GTTTACTCAT
     TGCCCCTCAG TCCGTTGATA CCTACTTGCT TTATCTGTCT AGCGACTCTA TCCACGGAGT GACTAATTCG TAACCATTGA CAGTCTGGTT CAAATGAGTA hphI
                                                   rmaI       sau3AI
                                                   sau3AI     mboI/ndeII[dam-]
                                                   mboI/ndeII[dam-]
                                                   dpnI[dam+]    dpnI[dam+]
                                       tru9I       dpnII[dam-]   dpnII[dam-]
                                       mseI        bstYI/xhoI    bstYI/xhoI                          nlaIII
                              tru9I    ahaIII/draI maeI          alwI[dam-]                          rcaI     tru9I
                              mseI                                                                   bspHI    mseI
                              ahaIII/draI
6201 ATATACTTTA GATTGATTTA AAACTTCATT TTTAATTTAA AAGGATCTAG GTGAAGATCC TTTTTGATAA TCTCATGACC AAAATCCCTT AACGTGAGTT
     TATATGAAAT CTAACTAAAT TTTGAAGTAA AAATTAAATT TTCCTAGATC CACTTCTAGG AAAAACTATT AGAGTACTGG TTTAGGGAA TTGCACTCAA sau3AI
                                                   mboI/ndeII[dam-]
                                                   dpnI[dam+]    sau3AI         thaI
                                                   dpnII[dam-]   mboI/ndeII[dam-]
                                                   bstYI/xhoI   dpnI[dam+]      fnuDII/mvnI
                                                   alwI[dam-]   dpnII[dam-]     bstUI
                                         sau3AI                  alwI[dam-]      bsh1236I
                                         mboI/ndeII[dam-]                       hinPI              fnu4HI
                                         dpnI[dam+] mboII[dam-]                 hhaI/cfoI          bbvI
                         ddeI hgaI       dpnII-dam-]              bstYI/xhoI
6301 TTCGTTCCAC TGAGCGTCAG ACCCCGTAGA AAAGATCAAA GGATCTTCTT GAGATCCTTT TTTTCTGCGC GTAATCTGCT GCTTGCAAAC AAAAAAACCA
     AAGCAAGGTG ACTCGCAGTC TGGGGCATCT TTTCTAGTTT CCTAGAAGAA CTCTAGGAAA AAAAGACGCG CATTAGACGA CGAACGTTTG TTTTTTTGGT
```

```
                    sau3AI
                    mboI/ndeII[dam-]
                    dpnI[dam+]
                    dpnII[dam-]
                    alwI[dam-]
        aciI        mspI                                                              bsrI         hinPI            rmaI
   aciI nspBII      hpaII      aluI                           maeII       eco57I                   hhaI/cfoI        maeI
6401 CCGCTACCAG CGGTGGTTTG TTTGCCGGAT CAAGAGCTAC CAACTCTTTT TCCGAAGGTA ACTGGCTTCA GCAGAGCGCA GATACCAAAT ACTGTCCTTC
     GGCGATGGTC GCCACCAAAC AAACGGCCTA GTTCTCGATG GTTGAGAAAA AGGCTTCCAT TGACCGAAGT CGTCTCGCGT CTATGGTTTA TGACAGGAAG
                                                                                                       fnu4HI
                                                                                                alwNI  bbvI
            haeIII/palI                                                                         bsrI   fnu4HI  bsrI
       bslI      haeI                       scfI       aciI         mnlI                        maeIII bbvI    bsaWI
6501 TAGTGTAGCC GTAGTTAGCC CACCACTTCA AGAACTCTGT AGCACCGCCT ACATACCTGG CTCTGCTAAT CCTGTTACCA GTGGCTGCTG CCAGTGGCGA
     ATCACATCGG CATCAATCGG GTGGTGAAGT TCTTGAGACA TCGTGGCGGA TGTATGGACC GAGACGATTA GGACAATGGT CACCGACGAC GGTCACCGCT
        scrFI                                                                mcrI                hgiAI/aspHI
        nciI                                                                 nspBII              bsp1286
        mspI                                                   mspI          fnu4HI              bsiHKAI
        hpszii                                                 hpaII         bbvI                bmyI
        dsaV       pleI                                        bsaWI         hinPI aciI          apaLI/snoI
        caUII      hinfI                       maeIII                        hhaI/cfoI           alw44I/snoI    aluI
6601 TAAGTCGTGT CTTACCGGGT TGGACTCAAG ACGATAGTTA CCGGATAAGG CGCAGCGGTC GGGCTGAACG GGGGGTTCGT GCACACAGCC CAGCTTGGAG
     ATTCAGCACA GAATGGCCCA ACCTGAGTTC TGCTATCAAT GGCCTATTCC GCGTCGCCAG CCCGACTTGC CCCCAAGCA CGTGTGTCGG GTCGAACCTC
                                                                              hinPI                  mspI
                                                                              hhaI/cfoI              bpaII
                ddeI       scfI                                               haeII                  bslI    fnu4HI
6701 CGAACGACCT ACACCGAACT GAGATACCTA CAGCGTGAGC ATTGAGAAAG CGCCACGCTT CCCGAAGGGA GAAAGGCGGA CAGGTATCCG GTAAGCGGCA
     GCTTGCTGGA TGTGGCTTGA CTCTATGGAT GTCGCACTCG TAACTCTTTC GCGGTGCGAA GGGCTTCCCT CTTTCCGCCT GTCCATAGGC CATTCGCCGT
                       scrFI                scrFI
                       mvaI                 mvaI
                       ecoRII   mvaI
                       dsaV     ecoRII      dsaV
                       bstNI                bstNI
                       bsaJI                apyI[dcm+]                                  mnlI drdI         taqI
     hinPI  mnlI                 aluI       apyI[dcm+]                                  hhaI/cfoI         hgaI
6801 GGGTCGGAAC AGGAGAGCGC ACGAGGGAGC TCCAGGGGGG AAACGCCTGG TATCTTTATA GTCCTGTCGG GTTTCGCCAC CTCTGACTTG AGCGTCGATT
     CCCAGCCTTG TCCTCTCGCG TGCTCCCTCG AAGGTCCCCC TTTGCGGACC ATAGAAATAT CAGGACAGCC CAAAGCGGTG GAGACTGAAC TCGCAGCTAA
```

```
                                                                              tru9I
                                                                              mseI
                                                       hinPI                  aseI/asnI/vspI
                       aluI                            hhaI/cfoI              
                       pvuII                    bsrI   aciI                   
          nlaIV        nspBII             bsrI  aciI   AAAGCGGGCA GTGAGCGCAA  CGCAATTAAT
  sfaNI   aciI  GGCGGAGCCT ATGAAAAAC GCCAGCTGGC ACGACAGGTT TCCCGACTGG AAAGCGGGCA GTGAGCGCAA CGCAATTAAT
6901 TTTGTGATGC TCGTCAGGGG GGCGGAGCCT ATGAAAAAAC GCCAGCTGGC ACGACAGGTT TCCCGACTGG AAAGCGGGCA GTGAGCGCAA CGCAATTAAT
     AAACACTACG AGCAGTCCCC CCGCCTCGGA TACCTTTTTG CGGTCGACCG TGCTGTCCAA AGGGCTGACC TTTCGCCCGT CACTCGCGTT GCGTTAATTA
                                                                ^delta1.PVU scrFI
                                     mvaI
                                     ecoRII
                                     dsaV
                              nlaIV  bstNI                                     mspI                            aciI
                  mnlI        hgiCI  apyI[dcm+]                                hpaII                           bsrBI
          maeIII              banI   bsaJI
7001 GTGAGTTACC TCACTCATTA GGCACCCCAG GCTTTACACT TTATGCTTCC GGCTCGTATG TTGTGTGGAA TTGTGAGCGG ATAACAATTT CACACAGGAA
     CACTCAATGG AGTGAGTAAT CCGTGGGGTC CGAAATGTGA AATACGAAGG CCGAGCATAC AACACACCTT AACACTCGCC TATTGTTAAA GTGTGTCCTT tru9I
                    mseI
                    aseI/asnI/vspI
                    xmnI
          aluI  nlaIII asp700
7101 ACAGCTATGA CCATGATTAC GAATTAA
     TGTCGATACT GGTACTAATG CTTAATT >lenth: 7127 aatII(GACGTC):       150 203 286 472 5182
```

*FIG. 5W*

OB PROTEIN-POLYMER CHIMERAS

This is a non-provisional application claiming priority under Section 119(e) to provisional application No. 60/040,911 filed Dec. 27, 1995.

FIELD OF THE INVENTION

The invention concerns long half-life variants of the OB protein. In particular, the invention concerns OB protein-immunoglobulin chimeras, and compositions comprising and methods for administering them. The invention further relates to a method for treating obesity by administering a long half-life variant of the OB protein, such as, an OB protein-immunoglobulin chimera.

BACKGROUND OF THE INVENTION

Obesity is the most common nutritional disorder which, according to recent epidemiologic studies, affects about one third of all Americans 20 years of age or older. Kuczmarski et al., *J. Am. Med. Assoc.* 272, 205–11 (1994). Obesity is responsible for a variety of serious health problems, including cardiovascular disorders, type II diabetes, insulin-resistance, hypertension, hypertriglyceridemia, dyslipoproteinemia, and some forms of cancer. Pi-Sunyer, F. X., *Anns. Int. Med.* 119, 655–60 (1993); Colfitz, G. A., *Am. J. Clin. Nutr.* 55, 503S–507S (1992). A single-gene mutation (the obesity or "ob" mutation) has been shown to result in obesity and type II diabetes in mice. Friedman, *Genomics* 11, 1054–1062 (1991). Zhang et al., *Nature* 372, 425–431 (1994) have recently reported the cloning and sequencing of the mouse ob gene and its human homologue, and suggested that the ob gene product may function as part of a signalling pathway from adipose tissue that acts to regulate the size of the body fat depot. Parabiosis experiments performed more than 20 years ago predicted that the genetically obese mouse containing two mutant copies of the ob gene (ob/ob mouse) does not produce a satiety factor which regulates its food intake, while the diabetic (db/db) mouse produces but does not respond to a satiety factor. Coleman and Hummal, *Am. J. Physiol.* 217, 1298–1304 (1969); Coleman, *Diabetol 9,* 294–98 (1973). Recent reports by three independent research teams have demonstrated that daily injections of recombinant OB protein inhibit food intake and reduce body weight and fat in grossly obese ob/ob mice but not in db/db mice (Pelleymounter et al., *Science* 269, 540–43 [1995]; Halaas et al., *Science* 269, 543–46 [1995]; Campfield et al., *Science* 269, 546–49 [1995]), suggesting that the ob protein is such a satiety factor as proposed in early cross-circulation studies. The results of these first studies leave many questions unanswered, and show a number of as yet unresolved discrepancies. For example, while modest effects of daily injections of the ob protein on food intake and body weight were reported in lean mice, there was a significant reduction in body fat as assessed by carcass composition in one (Halaas et al., supra) but not in another (Pelleymounter et al., supra) of these reports, despite equivalent decreases in body weight. Furthermore, Pelleymounteobobr et al., supra observed that, for reasons unknown, ob/ob mice treated with a 0.1 mg/kg/day dose of the OB protein actually increased their body weight by 17.13%, while the weight reduction in the obese mice that received a 1 mg/kg/day dose of ob was rather moderate. The receptor or receptors of the ob protein are as of yet unidentified. While the existence of peripheral receptors cannot be ruled out at this time, the recent report that an increased expression of the ob gene in adipose tissue of mice with hypothalamic lesions does not result in a lean phenotype suggests that the OB protein does not act directly on fat cells. Maffei et al., *Proc. Natl. Acad. Sci.* 92, 6957–60 (1995). Researchers suggest that at least one OB receptor is localized in the brain.

SUMMARY OF THE INVENTION

The present invention is based on the observation that the OB protein is significantly more effective at reducing body weight and adipose tissue weight when delivered as a continuous subcutaneous infusion than when the same dose is delivered as a daily subcutaneous injection. The invention is further based on the unexpected finding that a chimeric protein, in which the OB polypeptide is fused to an immunoglobulin constant domain, is strikingly more potent in reducing the body weight and adipose depots than native human OB, when both proteins are administered by subcutaneous injection once a day. The latter observation is particularly surprising since the OB protein—immunoglobulin chimera due to its large molecular weight, is not expected to be able to cross the blood-brain barrier, and reach the OB receptor which is believed to be located in the brain.

In one aspect, the invention concerns long half-life derivatives of OB proteins, compositions containing them, and their administration for the treatment of conditions associated with the abnormal expression or function of the OB gene, such as obesity.

In another aspect, the invention concerns chimeric polypeptides comprising an OB protein amino acid sequence capable of binding to a native OB receptor linked to an immunoglobulin sequence (briefly referred to as OB-immunoglobulin chimeras or immunoadhesins). In a specific embodiment, the chimeric polypeptides comprise a fusion of an OB amino acid sequence capable of binding a native OB receptor, to an immunoglobulin constant domain sequence. The OB portion of the chimeras of the present invention preferably has sufficient amino acid sequences from a native OB protein to retain the ability to bind to and signal through a native OB receptor. Most preferably, the OB protein retains the ability to reduce body weight when administered to obese human or non-human subjects. The OB polypeptide is preferably human, and the fusion is preferably with an immunoglobulin heavy chain constant domain sequence. In a particular embodiment, the association of two OB polypeptide-immunoglobulin heavy chain fusions (e.g., via covalent linkage by disulfide bond(s)) results in a homodimeric immunoglobulin-like structure. An immunoglobulin light chain may further be associated with one or both of the OB-immunoglobulin chimeras in the disulfide-bonded dimer to yield a homotrimeric or homotetrameric structure.

The invention further concerns nucleic acid encoding chimeric polypeptide chains of the present invention, expression vectors containing DNA encoding such molecules, transformed host cells, and methods for the production of the molecules by cultivating transformant host cells.

In another embodiment, the invention concerns a method of treating a condition associated with the abnormal expression or function of the OB gene by administering a therapeutically effective amount of a long half-life variant of an OB protein, such as an OB-immunoglobulin chimera. The invention specifically concerns a method of treating obesity.

In yet another embodiment, the invention concerns a composition for the treatment of a condition associated with the abnormal expression or function of a native OB gene, such as obesity, comprising an effective amount of a long half-life OB protein variant, such as an OB-immunoadhesin chimera.

BRIEF DESCRIPTION OF THE FIGURES

FIG. 1 top—Lean female mice were treated with murine OB protein either as a continuous subcutaneous infusion or daily subcutaneous injections. The data shown are the mean body weight of each group, in grams, n=4 mice/point.

FIG. 1 bottom—The mean weight of the retroperitoneal fat pads are shown. Continuous subcutaneous infusions of the OB protein were also more effective than daily subcutaneous injections at reducing adipose tissue weight.

FIG. 2 bottom—The data shown were the mean food intake for each treatment group for the six 24 hour periods of the experiment, in grams/mouse/day, n=1/bar.

FIG. 3 top and bottom—Obese (ob/ob) female mice were treated with either hOB or the hOB-IgG-1 fusion protein by daily subcutaneous injections for 7 days. The data are depicted as in FIG. 2, with n=4 for all treatment groups.

FIG. 4 top—Obese female ob/ob mice were treated with human protein (hOB) or with PEG-hOB. The data shown are the mean change in body weight for each treatment group from the first to the last day of experiment, in grams, n=3–4 mice/bar except for the PBS injection group, where n=1. The materials were injected daily subcutaneously. The "PEG 1×" and "PEG 2×" refer to the ratio of the PEG reagent to protein in the preparation of the molecule.

FIG. 4 bottom—The data shown were the mean food intake for each treatment group for the six 24 hour periods of the experiment, in grams/mouse/day, n=3–4/bar.

Figure 5C:
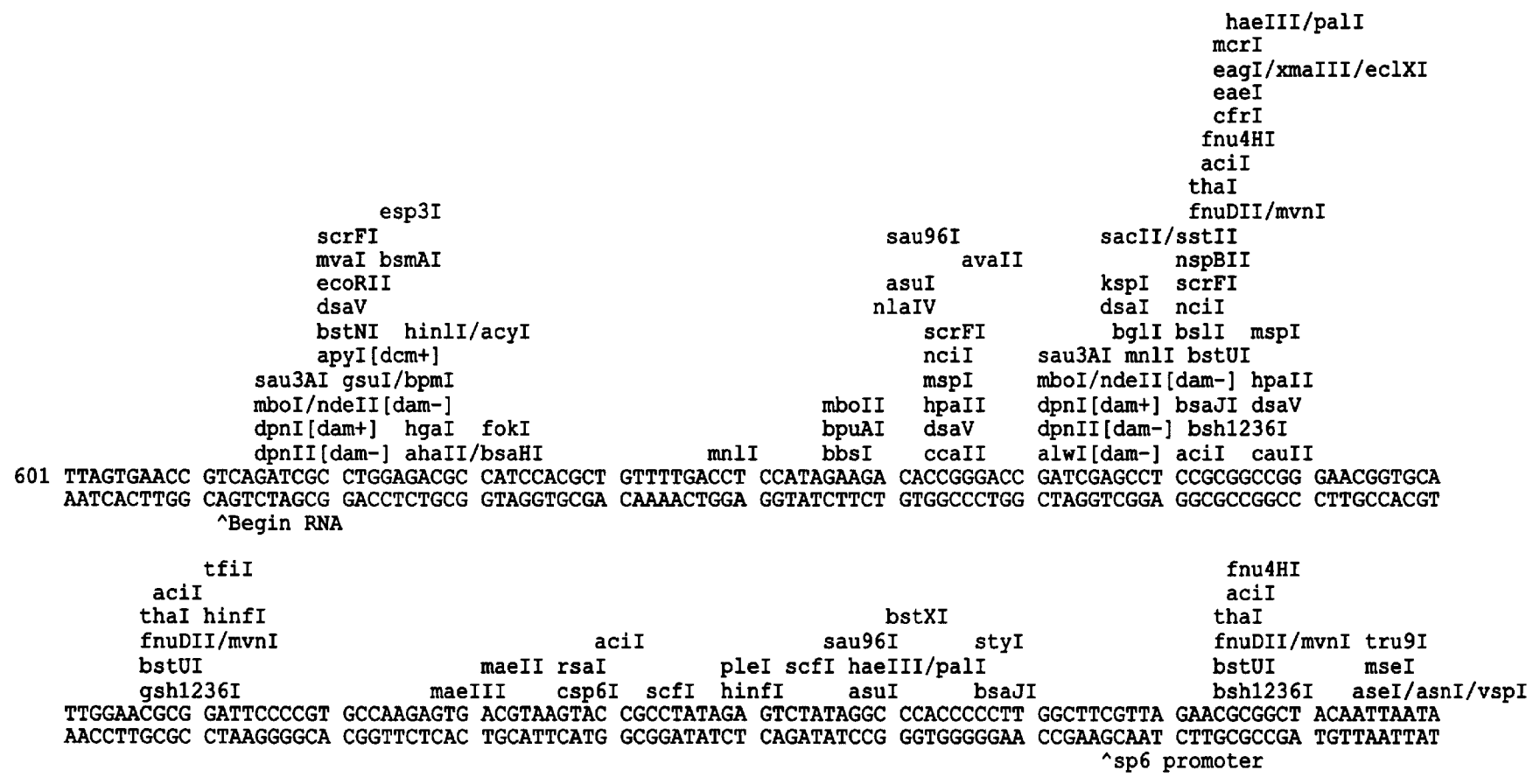
Figure 5E:
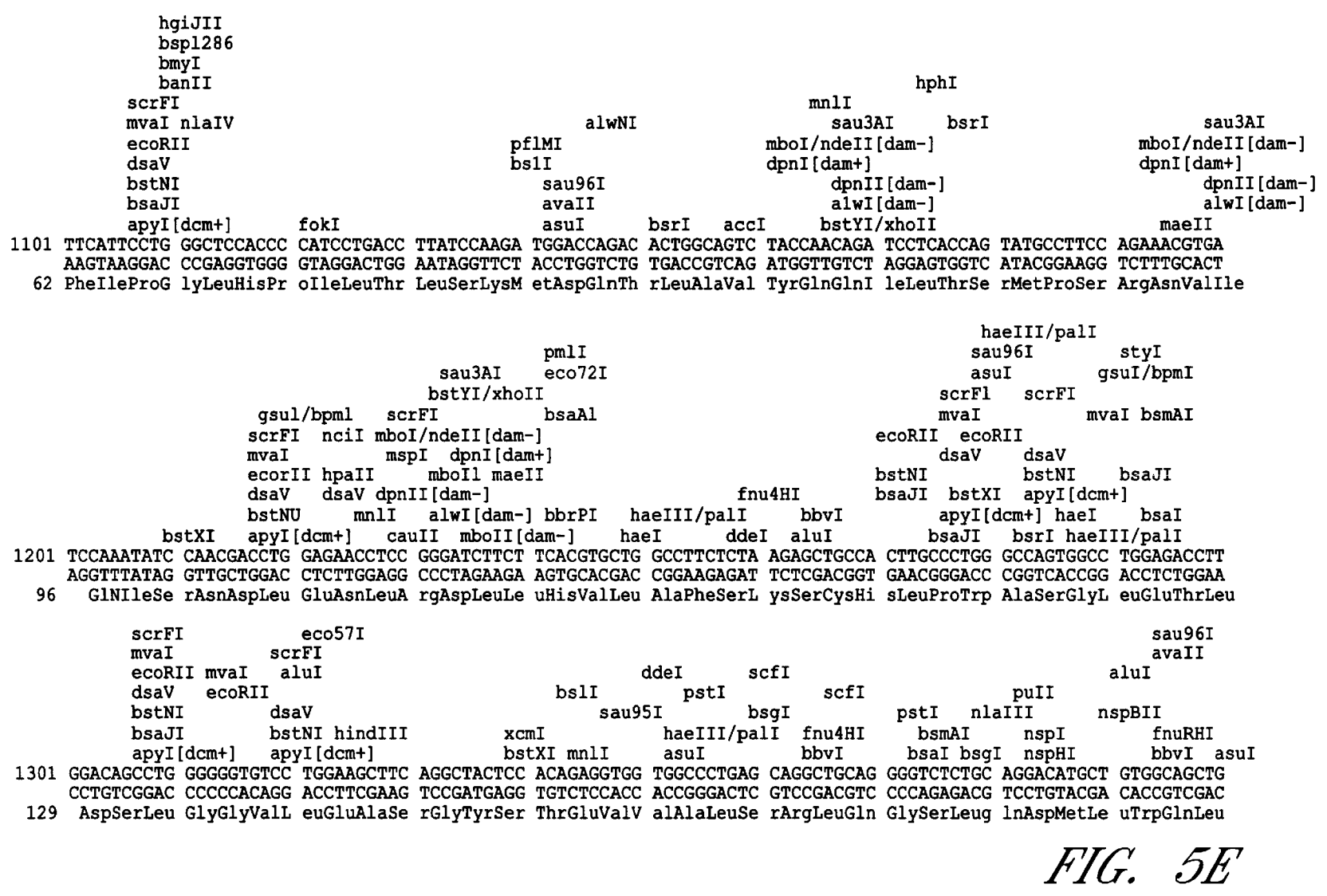
Figure 5F:
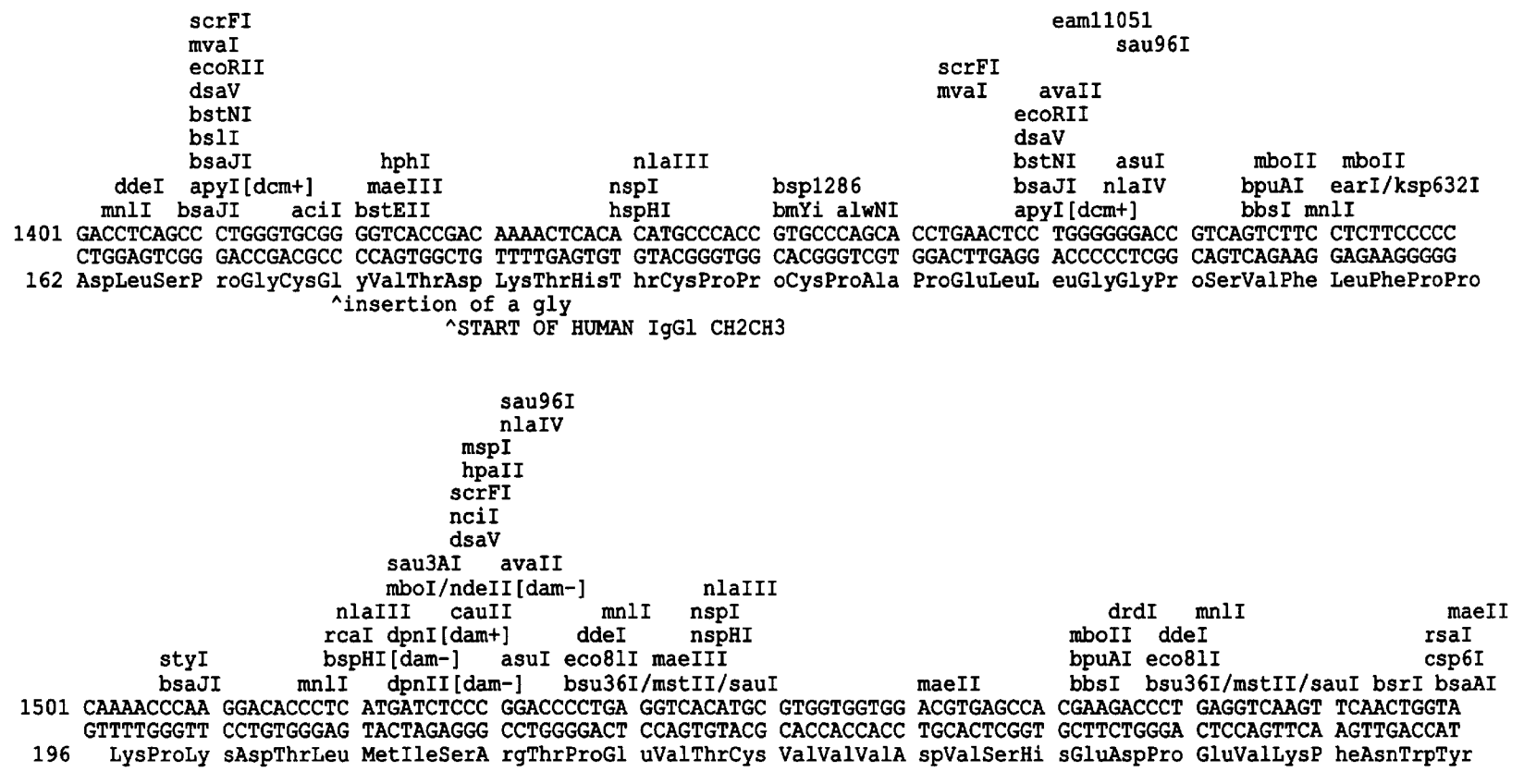
Figure 5K:
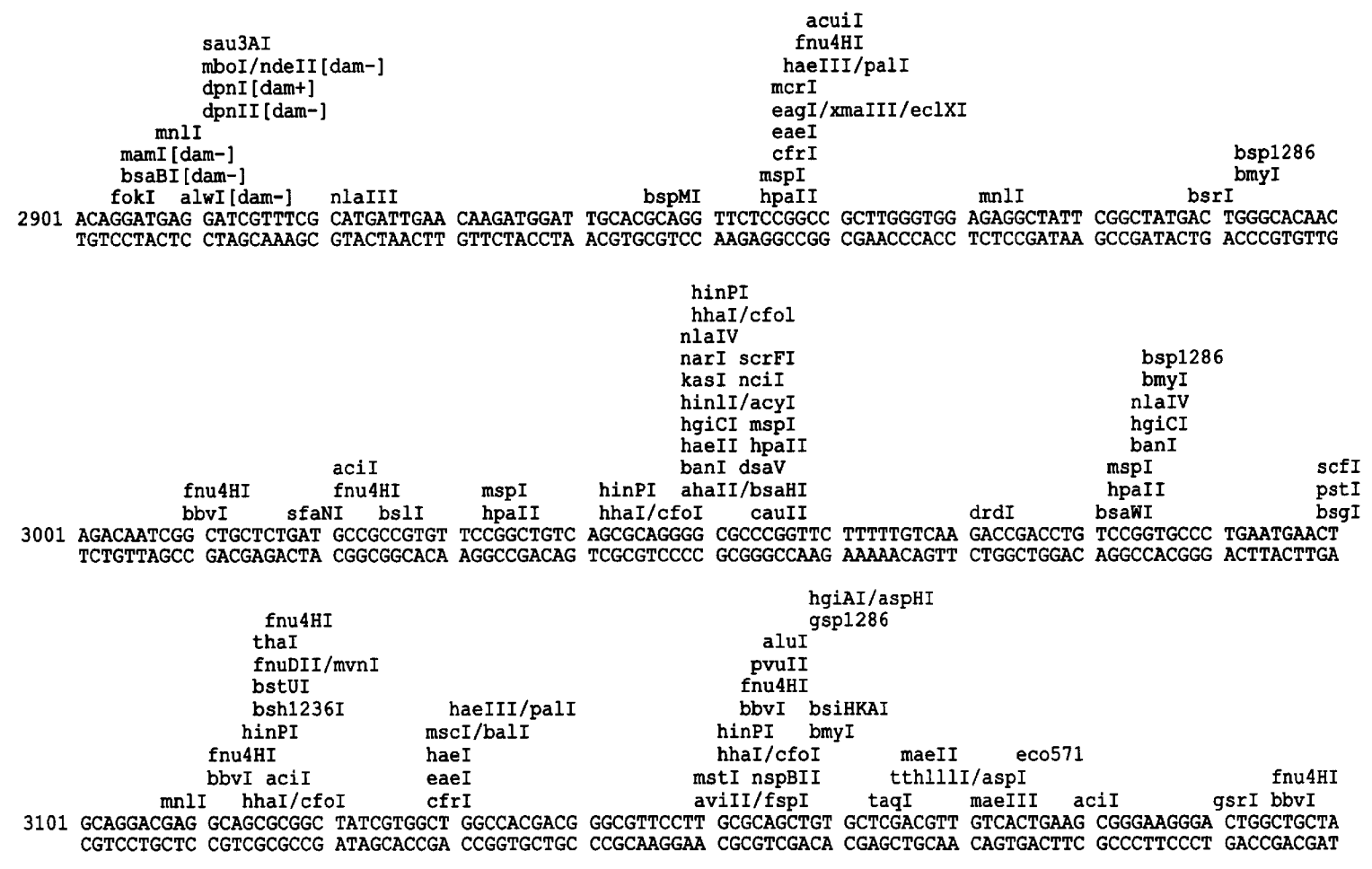
Figure 5R:
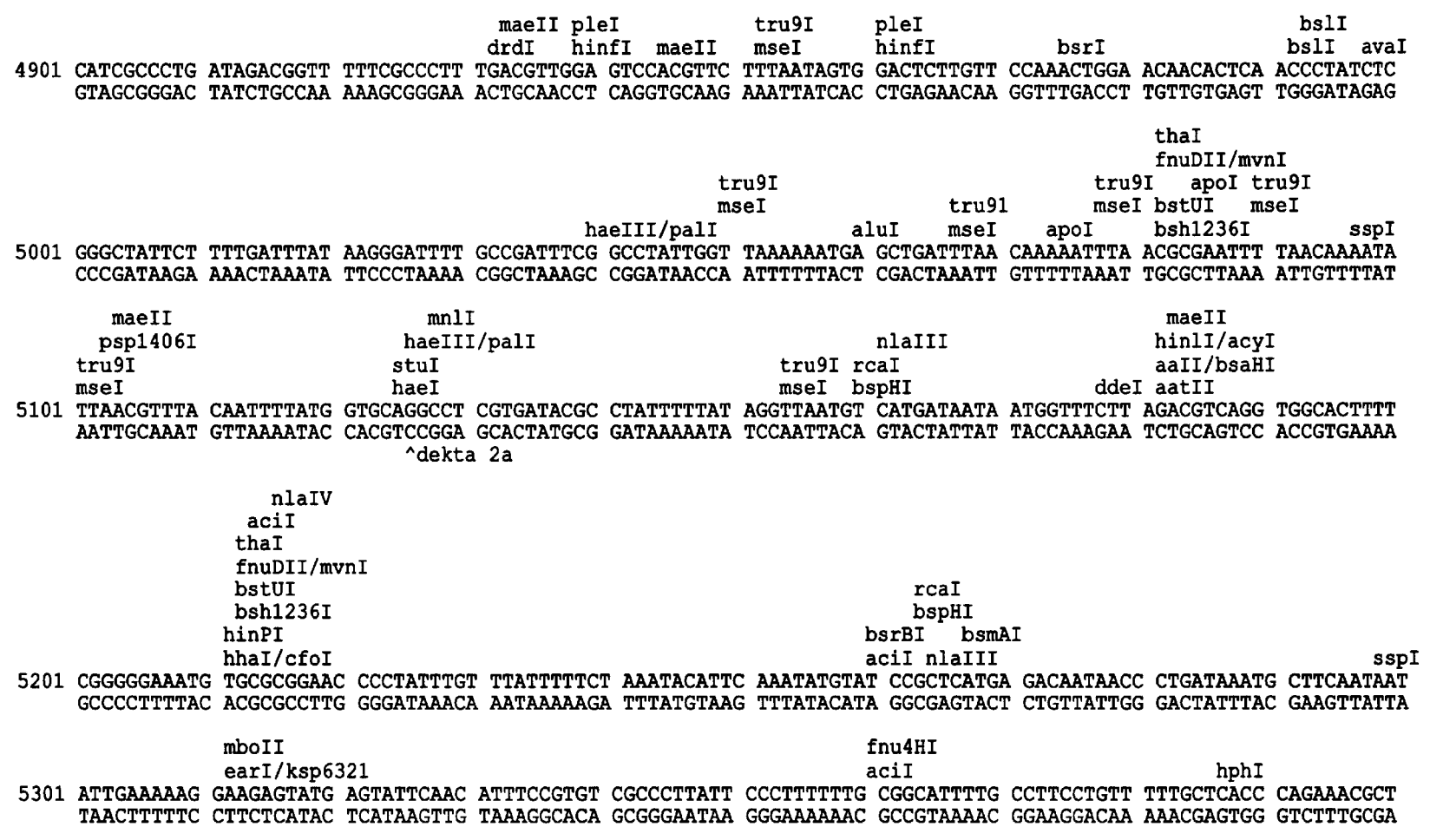

FIG. 5—The nucleotide sequence (SEQ. ID. NO:1) and the amino acid sequence (SEQ. ID. NO: 2) of the human OB-IgG-1 chimera of Example 1.

DETAILED DESCRIPTION OF THE INVENTION

A. Definitions

Figure 2:
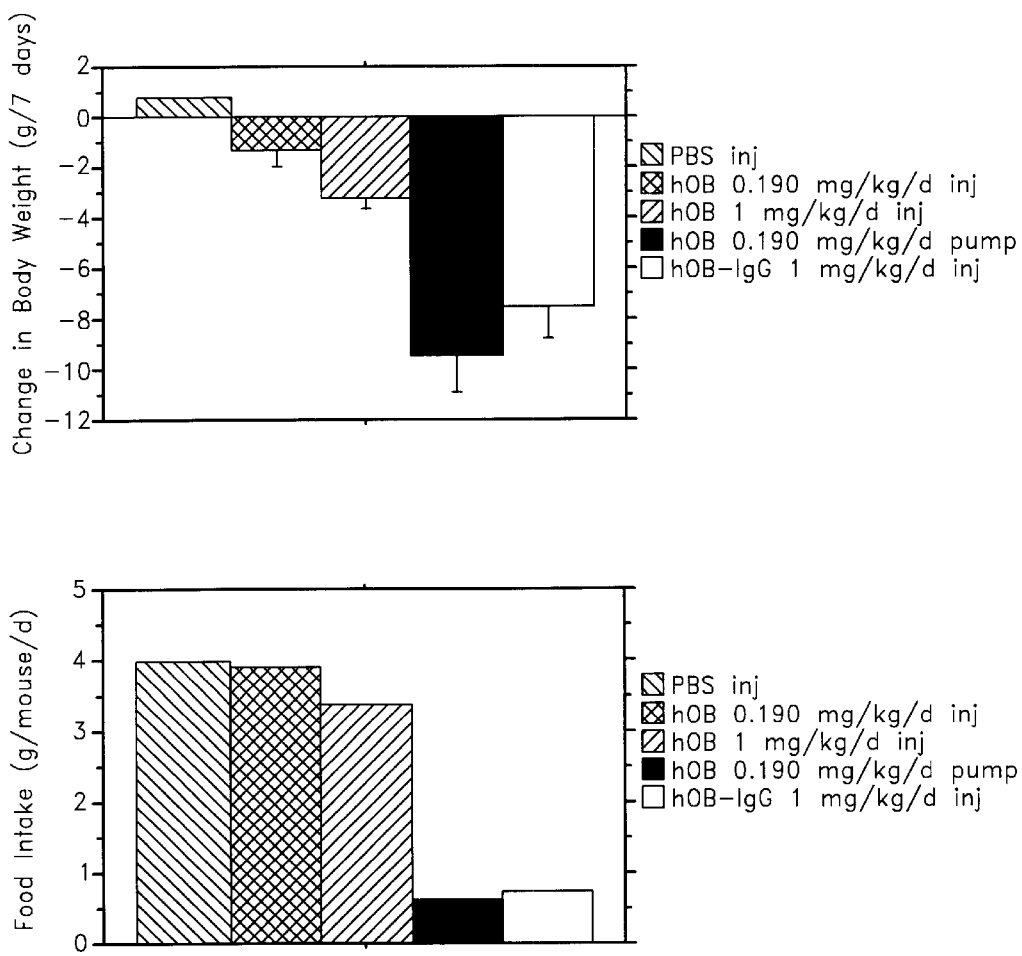
FIG. 2 top—Obese female ob/ob mice were treated with human OB protein (hOB) or with a human OB-IgG-1 fusion protein (hOB-IgG-1). The data shown are the mean change in body weight for each treatment group from the first to the last day of experiment, in grams, n=3 mice/bar except for the hOB 0.19 mg/kg/day by injection group, where n=4, and PBS injection group, where n=1.

The term "obesity" is used to designate a condition of being overweight associated with excessive bodily fat. The desirable weight for a certain individual depends on a number of factors including sex, height, age, overall built, etc. The same factors will determine when an individual is considered obese. The determination of an optimum body weight for a given individual is well within the skill of an ordinary physician.

The phrase "long half-life" and grammatical variants thereof, as used in connection with OB derivatives, concerns OB derivatives having a longer plasma half-life and/or slower clearance than a corresponding native OB protein. The long half-life derivatives preferably will have a half-life at least about 1.5-times longer than a native OB protein; more preferably at least about 2-times longer than a native OB protein, more preferably at least about 3-time longer than a native OB protein. The native OB protein preferably is that of the individual to be treated.

The terms "OB", "OB polypeptide", "OB protein" and their grammatical variants are used interchangeably and refer to "native" or "native sequence" OB proteins (also known as "leptins") and their functional derivatives. The OB polypeptides have the typical structural features of cytokines, i.e. polypeptides released by one cell population which act on another cell as intercellular mediators, such as, for example, growth hormones, insulin-like growth factors, interleukins, insulin, glycoprotein hormones such as, follicle stimulating hormone (FSH), thyroid stimulating hormone (TSH), tumor necrosis factor-α and -β (TNF-α and -β), nerve growth factors, such as NGF-β, PDGF, transforming growth factors (TGFs) such as, TGF-α and TGF-β, insulin-like growth factor-1 and -2 (IGF-1 and IGF-2), erythropoietin, osteoinductive factors, interferons (IFNs) such as, IFN-α, IFN-β and IFN-γ, colony stimulating factors (CSFs) such as, M-CSF, GM-CSF, and G-CSF, interleukins (ILs) such as, IL-1, IL-2, IL-3, IL-4, IL-5, IL-6, IL-7, IL-8 and other polypeptide factors.

The terms "native" and "native sequence" OB polypeptide are used to refer to an OB polypeptide from any animal species (e.g. human, murine, rabbit, cat, cow, sheep, chicken, porcine, equine, etc.), as occurring in nature, including naturally-occurring alleles, deletion, substitution and/or insertion variants, as currently known or as might be identified in the future, provided that they retain the ability to bind to and, preferably, signal through the OB receptor. Thus, a native human OB polypeptide includes the amino acid sequence between the N-terminus and the cysteine (Cys) at position 167 of the amino acid sequence shown in FIG. 5 (see also SEQ. ID. NO: 2 and FIG. 6 of Zhang et al., supra), and naturally occurring variants of this protein, as currently known or might be identified in the future. Similarly, a "native" or "native sequence" murine OB polypeptide has the amino acid sequence shown in FIG. 6 of Zhang et al., supra, and naturally occurring variants of that polypeptide, as currently known or might be identified in the future. The definition specifically includes variants with or without a glutamine at amino acid position 49, using the amino acid numbering of Zhang et al., supra. The terms "native" and "native sequence" OB polypeptide include the native proteins with or without the initiating N-terminal methionine (Met), and with or without the native signal sequence, either in monomeric or in dimeric form. The native human and murine OB polypeptides known in the art are 167 amino acids long, contain two conserved cysteines, and have the features of a secreted protein. The polypeptide is largely hydrophilic, and the predicted signal sequence cleavage site is at position 21, using the amino acid numbering of Zhang et al., supra. The overall sequence homology of the human and murine sequences is about 84%. The two proteins show a more extensive identity in the N-terminal region of the mature protein, with only four conservative and three non-conservative substitutions among the residues between the signal sequence cleavage site and the conserved Cys at position 117. The molecular weight of OB proteins is about 16 kD in a monomeric form.

A "functional derivative" of a native polypeptide is a compound having a qualitative biological property in common with the native polypeptide. A functional derivative of an OB polypeptide is a compound that has a qualitative biological property in common with a native (human or non-human) OB polypeptide. "Functional derivatives" include, but are not limited to, fragments of native polypeptides from any animal species (including humans), and derivatives of native (human and non-human) polypeptides and their fragments, provided that they have a biological activity in common with a corresponding native polypeptide.

"Fragments" comprise regions within the sequence of a mature native OB polypeptide. Preferred fragments of OB polypeptides include the C-terminus of the mature protein, and may contain relatively short deletion(s) at the N-terminus and in other parts of the molecule not required for receptor binding and/or for structural integrity.

The term "derivative" is used to define amino acid sequence variants, and covalent modifications of a native polypeptide, whereas the term "variant" refers to amino acid sequence variants within this definition.

"Biological property" in the context of the definition of "functional derivatives" is defined as either 1) immunological cross-reactivity with at least one epitope of a native polypeptide (e.g. a native OB polypeptide of any species), or 2) the possession of at least one adhesive, regulatory or effector function qualitatively in common with a native polypeptide.

Preferably, the functional derivatives are polypeptides which have at least about 65% amino acid sequence identity, more preferably about 75% amino acid sequence identity, even more preferably at least about 85% amino acid sequence identity, most preferably at least about 95% amino acid sequence identity with a native polypeptide. In the context of the present invention, functional derivatives of native sequence human OB polypeptides preferably show at least 95% amino acid sequence identity with the native OB proteins, and are not immunogenic in the human.

Amino acid sequence identity or homology is defined herein as the percentage of amino acid residues in the candidate sequence that are identical with the residues of a corresponding native polypeptide sequence, after aligning the sequences and introducing gaps, if necessary, to achieve the maximum percent homology, and not considering any conservative substitutions as part of the sequence identity. Neither N- or C-terminal extensions nor insertions shall be construed as reducing identity or homology.

Immunologically cross-reactive as used herein means that the candidate (poly)peptide is capable of competitively inhibiting the qualitative biological activity of a corresponding native polypeptide having this activity with polyclonal antibodies or antisera raised against the known active molecule. Such antibodies and antisera are prepared in conventional fashion by injecting an animal such as a goat or rabbit, for example, subcutaneously with the known native OB protein in complete Freud's adjuvant, followed by booster intraperitoneal or subcutaneous injection in incomplete Freud's.

The term "isolated OB polypeptide" and grammatical variants thereof refer to OB polypeptides (as hereinabove defined) separated from contaminant polypeptides present in the human, other animal species, or in other source from which the polypeptide is isolated.

In general, the term "amino acid sequence variant" refers to molecules with some differences in their amino acid sequences as compared to a reference (e.g. native sequence) polypeptide. The amino acid alterations may be substitutions, insertions, deletions or any desired combinations of such changes in a native amino acid sequence.

Substitutional variants are those that have at least one amino acid residue in a native sequence removed and a different amino acid inserted in its place at the same position. The substitutions may be single, where only one amino acid in the molecule has been substituted, or they may be multiple, where two or more amino acids have been substituted in the same molecule.

Insertional variants are those with one or more amino acids inserted immediately adjacent to an amino acid at a particular position in a native amino acid sequence. Immediately adjacent to an amino acid means connected to either the α-carboxy or α-amino functional group of the amino acid.

Deletional variants are those with one or more amino acids in the native amino acid sequence removed. Ordinarily, deletional variants will have one or two amino acids deleted in a particular region of the molecule.

"Covalent derivatives" include modifications of a native polypeptide or a fragment thereof with an organic proteinaceous or non-proteinaceous derivatizing agent, and post-translational modifications. Covalent modifications are traditionally introduced by reacting targeted amino acid residues with an organic derivatizing agent that is capable of reacting with selected sides or terminal residues, or by harnessing mechanisms of post-translational modifications that function in selected recombinant host cells. Certain post-transitional modifications are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Either form of these residues may be present in the OB-immunoglobulin chimeras of the present invention. Other post-translational modifications include hydroxylation of proline and lysine, phosphorylation of hydroxyl groups of seryl, tyrosine or threonyl residues, methylation of the α-amino groups of lysine, arginine, and histidine side chains [T. E. Creighton, *Proteins: Structure and Molecular Properties*, W. H. Freeman & Co., San Francisco, pp. 79–86 (1983)].

The terms "DNA sequence encoding", "DNA encoding" and "nucleic acid encoding" refer to the order or sequence of deoxyribonucleotides along a strand of deoxyribonucleic acid. The order of these deoxyribonucleotides determines the order of amino acids along the polypeptide chain. The DNA sequence thus codes for the amino acid sequence.

The terms "replicable expression vector" and "expression vector" refer to a piece of DNA, usually double-stranded, which may have inserted into it a piece of foreign DNA. Foreign DNA is defined as heterologous DNA, which is DNA not naturally found in the host cell. The vector is used to transport the foreign or heterologous DNA into a suitable host cell. Once in the host cell, the vector can replicate independently of the host chromosomal DNA, and several copies of the vector and its inserted (foreign) DNA may be generated. In addition, the vector contains the necessary elements that permit translating the foreign DNA into a polypeptide. Many molecules of the polypeptide encoded by the foreign DNA can thus be rapidly synthesized.

The term "control sequences" refers, to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancer.

Nucleic acid is "operably linked" when it is placed into a functional relationship with another nucleic acid sequence. For example, DNA for a presequence or a secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, then synthetic oligonucleotide adaptors or linkers are used in accord with conventional practice.

In the context of the present invention the expressions "cell", "cell line", and "cell culture" are used interchangeably, and all such designations include progeny. Thus, the words "transformants" and "transformed (host) cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

Native immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one and ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains (Clothia et al., *J. Mol. Biol.* 186, 651–663 (1985); Novotny and Haber, *Proc. Natl. Acad. Sci. USA* 82, 4592–4596 [1985]).

Depending on the amino acid sequence of the constant region of their heavy chains, immunoglobulins can be assigned to different classes. There are five major classes of immunoglobulins: IgA, IgD, IgE, IgG and IgM, and several of these may be further divided into subclasses (isotypes), e.g. IgG-1, IgG-2, IgG-3, and IgG-4; IgA-1 and IgA-2. The heavy chain constant regions that correspond to the different classes of immunoglobulins are called α, delta, epsilon, γ, and μ, respectively. The subunit structures and three-dimensional configurations of different classes of immunoglobulins are well known. IgA-1 and IgA-2 are monomeric subclasses of IgA, which usually is in the form of dimers or larger polymers. Immunocytes in the gut produce mainly polymeric IgA (also referred to poly-IgA including dimers and higher polymers). Such poly-IgA contains a disulfide-linked polypeptide called the "joining" or "J" chain, and can be transported through the glandular epithelium together with the J-containing polymeric IgM (poly-IgM), comprising five subunits.

Hybridization is preferably performed under "stringent conditions" which means (1) employing low ionic strength and high temperature for washing, for example, 0.015 sodium chloride/0.0015 M sodium citrate/0.1% sodium dodecyl sulfate at 50° C., or (2) employing during hybridization a denaturing agent, such as formamide, for example, 50% (vol/vol) formamide with 0.1% bovine serum albumin/0.1% Ficoll/0.1% polyvinylpyrrolidone/50 nM sodium phosphate buffer at pH 6.5 with 750 mM sodium chloride, 75 mM sodium citrate at 42° C. Another example is use of 50% formamide, 5×SSC (0.75 M NaCl, 0.075 M sodium citrate), 50 mM sodium phosphate (pH 6/8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC and 0.1% SDS.

B. OB Protein-immunoglobulin Chimeras (Immunoadhesins)

Immunoadhesins are chimeric antibody-like molecules that combine the functional domain(s) of a binding protein (usually a receptor, a cell-adhesion molecule or a ligand) with the an immunoglobulin sequence. The most common example of this type of fusion protein combines the hinge and Fc regions of an immunoglobulin (Ig) with domains of a cell-surface receptor that recognizes a specific ligand. This type of molecule is called an "immunoadhesin", because it combines "immune" and "adhesion" functions; other frequently used names are "Ig-chimera", "Ig- " or "Fc-fusion protein", or "receptor-globulin."

To date, more than fifty immunoadhesins have been reported in the art. Immunoadhesins reported in the literature include, for example, fusions of the T cell receptor (Gascoigne et al., *Proc. Natl. Acad. Sci. USA* 84, 2936–2940 [1987]); CD4 (Capon et al., *Nature* 337, 525–531 [1989]; Traunecker et al., *Nature* 339 68–70 [1989]; Zettmeissl et al., *DNA Cell Biol. USA* 9 347–353 [1990]; Byrn et al., *Nature* 344, 667–670 [1990]); L-selectin (homing receptor) (Watson et al., *J. Cell. Biol.* 110, 2221–2229 [1990]; Watson et al., *Nature* 349, 164–167 [1991]); E-selectin [Mulligan et al., *J. Immunol.* 151, 6410–17 [1993]; Jacob et al., *Biochemistry* 34, 1210–1217 [1995]); P-selectin (Mulligan et al., supra; Hollenbaugh et al., *Biochemistry* 34, 5678–84 [1995]); ICAM-1 (Stauton et al., *J. Exp. Med.* 176, 1471–1476 [1992]; Martin et al., *J. Virol.* 67, 3561–68 [1993]; Roep et al., *Lancet* 343, 1590–93 [1994]); ICAM-2 (Damle et al., *J. Immunol.* 148, 665–71 [1992]); ICAM-3 (Holness et al., *J. Biol. Chem.* 270, 877–84 [1995]); LFA-3 (Kanner et al., *J. Immunol.* 148, 2–23–29 [1992]); L1 glycoprotein (Doherty et al., *Neuron* 14, 57–66 [1995]); TNF-R1 (Ashkenazi et al., *Proc. Natl. Acad. Sci. USA* 88, 10535–539 [1991]; Lesslauer et al., *Eur. J. Immunol.* 21, 2883–86 [1991]; Peppel et al., *J. Exp. Med.* 174, 1483–1489 [1991]); TNF-R2 (Zack et al., *Proc. Natl. Acad. Sci. USA* 90, 2335–39 [1993]; Wooley et al., *J. Immunol.* 151, 6602–07 [1993]); CD44 [Aruffo et al., *Cell* 61, 1303–1313 (1990)]; CD28 and B7 [Linsley et al., *J. Exp. Med.* 173, 721–730 (1991)]; CTLA-4 [Lisley et al., *J. Exp. Med.* 174, 561–569 (1991)]; CD22 [Stamenkovic et al., *Cell* 66. 1133–1144 (1991)]; NP receptors [Bennett et al., *J. Biol. Chem.* 266, 23060–23067 (1991)]; IgE receptor α [Ridgway and Gorman, *J. Cell. Biol.* 115, abstr. 1448 (1991)]; HGF receptor [Mark, M. R. et al., 1992, *J. Biol. Chem.* submitted]; IFN-γR α- and β-chain [Marsters et al., *Proc. Natl. Acad. Sci. USA* 92, 5401–05 [1995]); trk-A, -B, and -C (Shelton et al., *J. Neurosci.* 15, 477–91 [1995]); IL-2 (Landolfi, *J. Immunol.* 146, 915–19 [1991]); IL-10 (Zheng et al., *J. Immunol.* 154, 5590–5600 [1995]).

The simplest and most straightforward immunoadhesin design combines the binding region(s) of the 'adhesin' protein with the hinge and Fc regions of an immunoglobulin heavy chain. Ordinarily, when preparing the OB-immunoglobulin chimeras of the present invention, nucleic acid encoding the desired OB polypeptide will be fused C-terminally to nucleic acid encoding the N-terminus of an immunoglobulin constant domain sequence, however N-terminal fusions are also possible. Typically, in such fusions the encoded chimeric polypeptide will retain at least functionally active hinge, CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain. The precise site at which the fusion is made is not critical; particular sites are well known and may be selected in order to optimize the biological activity, secretion or binding characteristics of the OB-immunoglobulin chimeras.

In a preferred embodiment, the sequence of a native, mature OB polypeptide, is fused to the N-terminus of the C-terminal portion of an antibody (in particular the Fc domain), containing the effector functions of an immunoglobulin, e.g. IgG-1. It is possible to fuse the entire heavy chain constant region to the OB sequence. However, more preferably, a sequence beginning in the hinge region just upstream of the papain cleavage site (which defines IgG Fc chemically; residue 216, taking the first residue of heavy chain constant region to be 114 [Kobet et al., supra], or analogous sites of other immunoglobulins) is used in the fusion. In a particularly preferred embodiment, the OB polypeptide sequence is fused to the hinge region and CH2 and CH3 or CH1, hinge, CH2 and CH3 domains of an IgG-1, IgG-2, or IgG-3 heavy chain. The precise site at which the fusion is made is not critical, and the optimal site can be determined by routine experimentation.

In some embodiments, the OB-immunoglobulin chimeras are assembled as multimers, and particularly as homodimers or -tetramers (WO 91/08298). Generally, these assembled immunoglobulins will have known unit structures. A basic four chain structural unit is the form in which IgG; IgD, and IgE exist. A four unit is repeated in the higher molecular weight immunoglobulins; IgM generally exists as a pentamer of basic four units held together by disulfide bonds. IgA globulin, and occasionally IgG globulin, may also exist in multimeric form in serum. In the case of multimer, each four unit may be the same or different.

Various exemplary assembled OB-immunoglobulin chimeras within the scope herein are schematically diagrammed below:

(a) $AC_L-AC_L$;
(b) $AC_H-[AC_H, AC_L-AC_H, AC_L-V_HC_H,$ or $V_LC_L-AC_H]$;
(c) $AC_L-AC_H-[AC_L-AC_H, AC_L-V_HC_H, V_LC_L-AC_H,$ or $V_LC_L-V_HC_H]$;
(d) $AC_L-V_HC_H-[AC_H,$ or $AC_L-V_HC_H,$ or $V_LC_L-AC_H]$;
(e) $V_LC_L-AC_H-[AC_L-V_HC_H,$ or $V_LC_L-AC_H]$; and
(f) $[A-Y]_n-[V_LC_L-V_HC_H]_2$, wherein
each A represents identical or different OB polypeptide amino acid sequences;
$V_L$ is an immunoglobulin light chain variable domain;
$V_H$ is an immunoglobulin heavy chain variable domain;
$C_L$ is an immunoglobulin light chain constant domain;
$C_H$ is an immunoglobulin heavy chain constant domain;
n is an integer greater than 1;
Y designates the residue of a covalent cross-linking agent.

In the interests of brevity, the foregoing structures only show key features; they do not indicate joining (J) or other domains of the immunoglobulins, nor are disulfide bonds shown. However, where such domains are required for binding activity, they shall be constructed as being present in the ordinary locations which they occupy in the immunoglobulin molecules.

Alternatively, the OB amino acid sequences can be inserted between immunoglobulin heavy chain and light chain sequences such that an immunoglobulin comprising a chimeric heavy chain is obtained. In this embodiment, the OB polypeptide sequences are fused to the 3' end of an immunoglobulin heavy chain in each arm of an immunoglobulin, either between the hinge and the CH2 domain, or between the CH2 and CH3 domains. Similar constructs have been reported by Hoogenboom, H. R. et al., Mol. Immunol. 28, 1027–1037 (1991).

Although the presence of an immunoglobulin light chain is not required in the immunoadhesins of the present invention, an immunoglobulin light chain might be present either covalently associated to an OB protein-immunoglobulin heavy chain fusion polypeptide, or directly fused to the OB polypeptide. In the former case, DNA encoding an immunoglobulin light chain is typically coexpressed with the DNA encoding the OB-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs. Method suitable for the preparation of such structures are, for example, disclosed in U.S. Pat. No. 4,816,567 issued Mar. 28, 1989.

In a preferred embodiment, the immunoglobulin sequences used in the construction of the immunoadhesins of the present invention are from an IgG immunoglobulin heavy chain constant domain. For human immunoadhesins, the use of human IgG-1 and IgG-3 immunoglobulin sequences is preferred. A major advantage of using IgG-1 is that IgG-1 immunoadhesins can be purified efficiently on immobilized protein A. In contrast, purification of IgG-3 requires protein G, a significantly less versatile medium. However, other structural and functional properties of immunoglobulins should be considered when choosing the Ig fusion partner for a particular immunoadhesin construction. For example, the IgG-3 hinge is longer and more flexible, so it can accommodate larger 'adhesin' domains that may not fold or function properly when fused to IgG-1. Possible IgG-based immunoadhesin structures are shown in FIGS. 3a–c. While IgG immunoadhesins are typically mono- or bivalent, other Ig subtypes like IgA and IgM may give rise to dimeric or pentameric structures, respectively, of the basic Ig homodimer unit. A typical IgM-based multimeric immunoadhesin is illustrated in FIG. 3d. Multimeric immunoadhesins are advantageous in that they can bind their respective targets with greater avidity than their IgG-based counterparts. Reported examples of such structures are CD4-IgM (Traunecker et al., supra); ICAM-IgM (Martin et al., J. Virol. 67, 3561–68 [1993]); and CD2-IgM (Arulanandam et al., J. Exp. Med. 177, 1439–50 [1993]).

For OB-Ig immunoadhesins, which are designed for in vivo application, the pharmacokinetic properties and the effector functions specified by the Fc region are important as well. Although IgG-1, IgG-2 and IgG-4 all have in vivo half-lives of 21 days, their relative potencies at activating the complement system are different. IgG-4 does not activate complement, and IgG-2 is significantly weaker at complement activation than IgG-1. Moreover, unlike IgG-1, IgG-2 does not bind to Fc receptors on mononuclear cells or neutrophils. While IgG-3 is optimal for complement activation, its in vivo half-life is approximately one third of the other IgG isotypes. Another important consideration for immunoadhesins designed to be used as human therapeutics is the number of allotypic variants of the particular isotype. In general, IgG isotypes with fewer serologically-defined allotypes are preferred. For example, IgG-1 has only four serologically-defined allotypic sites, two of which (G1m and 2) are located in the Fc region; and one of these sites G1m1, is non-immunogenic. In contrast, there are 12 serologically-defined allotypes in IgG-3, all of which are in the Fc region;

only three of these sites (G3m5, 11 and 21) have one allotype which is nonimmunogenic. Thus, the potential immunogenicity of a γ3 immunoadhesin is greater than that of a γ1 immunoadhesin.

In designing the OB-Ig immunoadhesins of the present invention regions that are not required for receptor binding, the structural integrity (e.g. proper folding) and/or biological activity of the molecule, may be deleted. In such structures, it is important to place the fusion junction at residues that are located between domains, to avoid misfolding. With respect to the parental immunoglobulin, a useful joining point is just upstream of the cysteines of the hinge that form the disulfide bonds between the two heavy chains. In a frequently used design, the codon for the C-terminal residue of the "adhesin" (OB) part of the molecule is placed directly upstream of the codons for the sequence DKTHTCPPCP of the IgG1 hinge region.

OB-Ig immunoadhesins are most conveniently constructed by fusing the cDNA sequence encoding the OB portion in-frame to an Ig cDNA sequence. However, fusion to genomic Ig fragments can also be used (see, e.g. Gascoigne et al., *Proc. Natl. Acad. Sci. USA* 84, 2936–2940 [1987]; Aruffo et al., *Cell* 61, 1303–1313 [1990]; Stamenkovic et al., *Cell* 66, 1133–1144 [1991]). The latter type of fusion requires the presence of Ig regulatory sequences for expression. cDNAs encoding IgG heavy-chain constant regions can be isolated based on published sequence from cDNA libraries derived from spleen or peripheral blood lymphocytes, by hybridization or by polymerase chain reaction (PCR) techniques. Murine OB cDNA can, for example, be obtained by PCR from a mouse adipose tissue cDNA library (Clontech), using primers designed based on the sequence of Zhang et al. Human OB cDNA can be obtained in a similar manner. Alternatively, the mouse OB gene can be used as a probe to isolate human adipose tissue cDNA clones (Clontech), e.g. from a λgtII library, as described by Zhang et al. The cDNAs encoding the 'adhesin' and the Ig parts of the immunoadhesin are inserted in tandem into a plasmid vector that directs efficient expression in the chosen host cells. For expression in mammalian cells pRK5-based vectors (Schall et al., *Cell* 61, 361–370 [1990]), pRK7-vectors and CDM8-based vectors (Seed, *Nature* 329, 840 [1989]) are preferred. (pRK7 is identical to pRK5 except that the order of the endonuclease restriction sites in the polylinker region between ClaI and HindIII is reversed. See U.S. Pat. No. 5,108,901 issued Apr. 28, 1992.). The exact junction can be created by removing the extra sequences between the designed junction codons using oligonucleotide-directed deletional mutagenesis (Zoller and Smith, *Nucleic Acids Res.* 10, 6487 [1982]; Capon et al., *Nature* 337, 525–531 [1989]). Synthetic oligonucleotides can be used, in which each half is complementary to the sequence on either side of the desired junction; ideally, these are 36 to 48-mers. Alternatively, PCR technique can be used to join the two parts of the molecule in-frame with an appropriate vector.

Immunoadhesins can be expressed efficiently in a variety of host-cells, including myeloma cell lines, Chinese Hamster ovary (CHO) cells, monkey COS cells, human embryonic kidney 293 cells, and baculovirus infected insect cells. In these systems, the immunoadhesin polypeptides are assembled and secreted into the cell culture medium. Yeasts, e.g. *Saccharomyces cerevisiae, Pichia pastoris*, etc., and bacterial cells, preferably *E. coli*, can also be used as hosts. The OB-immunoglobulin chimeras can be expressed in yeast, for example, similarly to the process described for the expression of the OB proteins by Leiber et al., *Crit. Res. Food Sci. Nutr.* 33, 351 (1993); Friedman and Leibel, *Cell* 69, 217 (1992); and Beavis and Chait, *Proc. Natl. Acad. Sci. USA* 87, 6873 (1990). Thus, the coding sequences can be subcloned into a yeast plasmid, such as the yeast expression plasmid pPIC.9 (Invitrogen). This vector directs secretion of heterologous proteins from the yeast into the culture media. According to Halaas et al., supra, expression of mouse and human OB genes in *Saccharomyces cerevisiae* transformed with this vector yields a secreted 16-kD protein, which is an unprocessed OB protein lacking the signal sequence. Expression of the mouse or human OB-immunoglobulin chimeras in *E. coli* can, for example, be performed on the analogy of the procedure described by Halaas et al., supra. The coding sequences of mouse and human OB-immunoglobulin chimeras can be subcloned into the PET15b expression vector (Novagen) and expressed in *E. coli* (BL21 (DE3)pIYsS) through use of the T7 *E. coli* RNA polymerase system. Alternatively, the fusion protein can be expressed in *E. coli* by inserting the coding sequence in frame with the secretion sequence of the *E. coli* heat stable enterotoxin II, downstream of the *E. coli* alkaline phosphatase promoter (Chang et al., *Gene* 55, 189–96 [1987]).

The choice of host cell line for the expression of OB-Ig immunoadhesins depends mainly on the expression vector. Another consideration is the amount of protein that is required. Milligram quantities often can be produced by transient transfections. For example, the adenovirus EIA-transformed 293 human embryonic kidney cell line can be transfected transiently with pRK5- and pRK7-based vectors by a modification of the calcium phosphate method to allow efficient immunoadhesin expression. This method is illustrated in the examples. CDM8-based vectors can be used to transfect COS cells by the DEAE-dextran method (Aruffo et al., *Cell* 61, 1303–1313 (1990); Zettmeissl et al., *DNA Cell Biol.* (US) 9, 347–353 (1990)]. If larger amounts of protein are desired, the immunoadhesin can be expressed after stable transfection of a host cell line. For example, a pRK5- or pRK7-based vector can be introduced into Chinese hamster ovary (CHO) cells in the presence of an additional plasmid encoding dihydrofolate reductase (DHFR) and conferring resistance to G418. Clones resistant to G418 can be selected in culture; these clones are grown in the presence of increasing levels of DHFR inhibitor methotrexate; clones are selected, in which the number of gene copies encoding the DHFR and immunoadhesin sequences is co-amplified. If the immunoadhesin contains a hydrophobic leader sequence at its N-terminus, it is likely to be processed and secreted by the transfected cells. The expression of immunoadhesins with more complex structures may require uniquely suited host cells; for example, components such as light chain or J chain may be provided by certain myeloma or hybridoma cell hosts [Gascoigne et al., 1987, supra; Martin et al., *J. Virol.* 67, 3561–3568 (1993)].

The expression of immunoadhesins with more complex oligomeric structures may require uniquely suited host cells; for example, components such as light chain or J chain may be provided by certain myeloma or hybridoma cell hosts (Gascoigne et al., supra; Martin et al., *J. Immunol.* 67, 3561–68 [1993]).

Immunoadhesins can be conveniently purified by affinity chromatography. The suitability of protein A as an affinity ligand depends on the species and isotype of the immunoglobulin Fc domain that is used in the chimera. Protein A can be used to purify immunoadhesins that are based on human γ1, γ2, or γ4 heavy chains [Lindmark et al., *J. Immunol. Meth.* 62, 1–13 (1983)]. Protein G is recommended for all mouse isotypes and for human γ3 [Guss et al., *EMBO J.* 5, 15671575 (1986)]. The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. The conditions for binding an immunoadhesin to the protein A or G affinity column are dictated entirely by the characteristics of the Fc domain; that is, its species and isotype. Generally, when the proper ligand is chosen, efficient binding occurs directly from unconditioned culture fluid. One distinguishing feature of immunoadhesins is that, for human γ1 molecules, the binding capacity for protein A is somewhat diminished relative to an antibody of the same Fc type. Bound immunoadhesin can be efficiently eluted either at acidic pH (at or above 3.0), or in a neutral pH buffer containing a mildly chaotropic salt. This affinity chromatography step can result in an immunoadhesin preparation that is >95% pure.

Other methods known in the art can be used in place of, or in addition to, affinity chromatography on protein A or G to purify immunoadhesins. Immunoadhesins behave similarly to antibodies in thiophilic gel chromatography [Hutchens and Porath, *Anal. Biochem.* 159, 217–226 (1986)] and immobilized metal chelate chromatography [Al-Mashikhi and Makai, *J. Dairy Sci.* 71, 1756–1763 (1988)]. In contrast to antibodies, however, their behavior on ion exchange columns is dictated not only by their isoelectric points, but also by a charge dipole that may exist in the molecules due to their chimeric nature. Microheterogeneity of charge can also be a factor for immunoadhesins in which the adhesin portion of the molecule is glycosylated and contains sialic acid. A specific purification protocol is described in the examples.

Results with the numerous immunoadhesins produced so far show that the fusion of the adhesin portion to an Fc region usually does not perturb the folding of the individual domains. Both the adhesin and the immunoglobulin regions appear to fold correctly, and the Fc portion retins many of the effector functions that are characteristic of antibodies, such as binding to Fc receptors.

Methods generally applicable for the construction, expression and purification of immunoadhesins are described, for example, in U.S. Pat. Nos. 5,225,538 (issued Jul. 6, 1993) and U.S. Pat. No. 5,455,165 (issued Oct. 30, 1995), the disclosures of which are hereby expressly incorporated by reference. Immunoadhesin construction, expression, purification and various immunoadhesins designs are also described in the review articles by Ashkenazi and Chamow, *Methods in Enzymology* 8, 104–115 (1995), and Peach and Linsley, *Methods in Enzymology* 8, 116–123 (1995), the disclosures of which, along with the references cited therein, is hereby expressly incorporated by reference.

C. Other Long Half-life OB Derivatives

Other derivatives of the OB proteins, which possess a longer half-life than the native molecules comprise the OB protein or an OB-immunoglobulin chimera, covalently bonded to a nonproteinaceous polymer. The nonproteinaceous polymer ordinarily is a hydrophilic synthetic polymer, i.e., a polymer not otherwise found in nature. However, polymers which exist in nature and are produced by recombinant or in vitro methods are useful, as are polymers which are isolated from native sources. Hydrophilic polyvinyl polymers fall within the scope of this invention, e.g. polyvinylalcohol and polyvinylpyrrolidone. Particularly useful are polyalkylene ethers such as polyethylene glycol (PEG); polyelkylenes such as polyoxyethylene, polyoxypropylene, and block copolymers of polyoxyethylene and polyoxypropylene (Pluronics); polymethacrylates; carbomers; branched or unbranched polysaccharides which comprise the saccharide monomers D-mannose, D- and L-galactose, fucose, fructose, D-xylose, L-arabinose, D-glucuronic acid, sialic acid, D-galacturonic acid, D-mannuronic acid (e.g. polymannuronic acid, or alginic acid), D-glucosamine, D-galactosamine, D-glucose and neuraminic acid including homopolysaccharides and heteropolysaccharides such as lactose, amylopectin, starch, hydroxyethyl starch, amylose, dextrane sulfate, dextran, dextrins, glycogen, or the polysaccharide subunit of acid mucopolysaccharides, e.g. hyaluronic acid; polymers of sugar alcohols such as polysorbitol and polymannitol; heparin or heparon. The polymer prior to cross-linking need not be, but preferably is, water soluble, but the final conjugate must be water soluble. In addition, the polymer should not be highly immunogenic in the conjugate form, nor should it possess viscosity that is incompatible with intravenous infusion or injection if it is intended to be administered by such routes.

Preferably the polymer contains only a single group which is reactive. This helps to avoid cross-linking of protein molecules. However, it is within the scope herein to optimize reaction conditions to reduce cross-linking, or to purify the reaction products through gel filtration or chromatographic sieves to recover substantially homogenous derivatives.

The molecular weight of the polymer may desirably range from about 100 to 500,000, and preferably is from about 1,000 to 20,000. The molecular weight chosen will depend upon the nature of the polymer and the degree of substitution. In general, the greater the hydrophilicity of the polymer and the greater the degree of substitution, the lower the molecular weight that can be employed. Optimal molecular weights will be determined by routine experimentation.

The polymer generally is covalently linked to the OB protein or to the OB-immunoglobulin chimeras though a multifunctional crosslinking agent which reacts with the polymer and one or more amino acid or sugar residues of the OB protein or OB-immunoglobulin chimera to be linked. However, it is within the scope of the invention to directly crosslink the polymer by reacting a derivatized polymer with the hybrid, or via versa.

The covalent crosslinking site on the OB protein or OB-Ig includes the N-terminal amino group and epsilon amino groups found on lysine residues, as well as other amino, imino, carboxyl, sulfhydryl, hydroxyl or other hydrophilic groups. The polymer may be covalently bonded directly to the hybrid without the use of a multifunctional (ordinarily bifunctional) crosslinking agent. Covalent binding to amino groups is accomplished by known chemistries based upon cyanuric chloride, carbonyl diimidazole, aldehyde reactive groups (PEG alkoxide plus diethyl acetal of bromoacetaldehyde; PEG plus DMSO and acetic anhydride, or PEG chloride plus the phenoxide of 4-hydroxybenzaldehyde, succinimidyl active esters, activated dithiocarbonate PEG, 2,4,5-trichlorophenylchloroformate or P-nitrophenylchloroformate activated PEG.) Carboxyl groups are derivatized by coupling PEG-amine using carbodiimide.

Polymers are conjugated to oligosaccharide groups by oxidation using chemicals, e.g. metaperiodate, or enzymes, e.g. glucose or galactose oxidase, (either of which produces the aldehyde derivative of the carbohydrate), followed by reaction with hydrazide or amino derivatized polymers, in the same fashion as is described by Heitzmann et al., *P.N.A.S.*, 71, 3537–41 (1974) or Bayer et al., *Methods in Enzymology* 62, 310 (1979), for the labeling of oligosaccharides with biotin or avidin. Further, other chemical or enzymatic methods which have been used heretofore to link oligosaccharides are particularly advantageous because, in general, there are fewer substitutions than amino acid sites for derivatization, and the oligosaccharide products thus will be more homogenous. The oligosaccharide substituents also are optionally modified by enzyme digestion to remove sugars, e.g. by neuraminidase digestion, prior to polymer derivatization.

The polymer will bear a group which is directly reactive with an amino acid side chain, or the N- or C-terminus of the polypeptide linked, or which is reactive with the multifunctional cross-linking agent. In general, polymers bearing such reactive groups are known for the preparation of immobilized proteins. In order to use such chemistries here, one should employ a water soluble polymer otherwise derivatized in the same fashion as insoluble polymers heretofore employed for protein immobilization. Cyanogen bromide activation is a particularly useful procedure to employ in crosslinking polysaccharides.

"Water soluble" in reference to the starting polymer means that the polymer or its reactive intermediate used for conjugation is sufficiently water soluble to participate in a derivatization reaction.

"Water soluble" in reference to the polymer conjugate means that the conjugate is soluble in physiological fluids such as blood.

The degree of substitution with such a polymer will vary depending upon the number of reactive sites on the protein, whether all or a fragment of the protein is used, whether the protein is a fusion with a heterologous protein (e.g. an OB-immunoglobulin chimera), the molecular weight, hydrophilicity and other characteristics of the polymer, and the particular protein derivatization sites chosen. In general, the conjugate contains about from 1 to 10 polymer molecules, while any heterologous sequence may be substituted with an essentially unlimited number of polymer molecules so long as the desired activity is not significantly adversely affected. The optimal degree of cross-linking is easily determined by an experimental matrix in which the time, temperature and other reaction conditions are varied to change the degree of substitution, after which the ability of the conjugates to function in the desired fashion is determined.

The polymer, e.g. PEG, is cross-linked by a wide variety of methods known per se for the covalent modification of proteins with nonproteinaceous polymers such as PEG. Certain of these methods, however, are not preferred for the purposes herein. Cyanuronic chloride chemistry leads to many side reactions, including protein cross-linking. In addition, it may be particularly likely to lead to inactivation of proteins containing sulfhydryl groups. Carbonyl diimidazole chemistry (Beauchamp et al., *Anal Biochem.* 131, 25–33 [1983]) requires high pH (>8.5), which can inactivate proteins. Moreover, since the "activated PEG" intermediate can react with water, a very large molar excess of "activated PEG" over protein is required. The high concentrations of PEG required for the carbonyl diimidazole chemistry also led to problems in purification, as both gel filtration chromatography and hydrophilic interaction chromatography are adversely affected. In addition, the high concentrations of "activated PEG" may precipitate protein, a problem that per se has been noted previously (Davis, U.S. Pat. No. 4,179, 337). On the other hand, aldehyde chemistry (Royer, U.S. Pat. No. 4,002,531) is more efficient since it requires only a 40-fold molar excess of PEG and a 1–2 hr incubation. However, the manganese dioxide suggested by Royer for preparation of the PEG aldehyde is problematic "because of the pronounced tendency of PEG to form complexes with metal-based oxidizing agents" (Harris et al., *J. Polym. Sci. Polym. Chem. Ed.* 22, 341–52 [1984]). The use of a Moffatt oxidation, utilizing DMSO and acetic anhydride, obviates this problem. In addition, the sodium borohydride suggested by Royer must be used at high pH and has a significant tendency to reduce disulfide bonds. In contrast, sodium cyanoborohydride, which is effective at neutral pH and has very little tendency to reduce disulfide bonds is preferred.

The long half-life conjugates of this invention are separated from the unreacted starting materials by gel filtration. Heterologous species of the conjugates are purified from one another in the same fashion. The polymer also may be water-insoluble, as a hydrophilic gel.

D. The Use of the OB-immunoglobulin Chimeras and Other Long half-life Derivatives The OB-immunoglobulin chimeras and other long half-life OB derivatives of the present invention are useful in the treatment of obesity and other disorders associated with the abnormal expression or function of the OB gene. Our studies indicate that the OB-immunoglobulin chimeras and other long half-life OB derivatives, e.g. PEGylated OB, reduce the food intake and increase the energy use of animals treated, and are therefore very effective in reducing the weight of both obese and normal subjects. For testing purposes, the molecules of the present invention may be dissolved in phosphate-buffered saline (PBS) (pH 7.4), and administered by intravenous or subcutaneous injection, or infusion.

Therapeutic formulations of the present invention are prepared for storage by mixing the active ingredient having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or PEG.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules) or in macroemulsions. Such techniques are disclosed in *Remington's Pharmaceutical Sciences*, supra.

The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, etc. routes. Sustained released formulations are also foreseen. Suitable examples of sustained release preparations include semipermeable polymer matrices in the form of shaped articles, e.g. films, or microcapsules. Sustained release matrices include polyesters, hydrogels, polylactides (U.S. Pat. No. 3,773,919, EP 58,48 1), copolymers of L-glutamic acid and gamma ethyl-L-glutamate (U. Sidman et al., 1983, "Biopolymers" 22 (1): 547–556), poly (2-hydroxyethyl-methacrylate) (R. Langer, et al., 1981, "J. Biomed. Mater. Res." 15: 167–277 and R. Langer, 1982, Chem. Tech." 12: 98–105), ethylene vinyl acetate (R. Langer et al., Id.) or poly-D-(-)-3-hydroxybutyric acid (EP 133, 988A). Sustained release compositions also include liposomes. Liposomes containing a molecule within the scope of the present invention are prepared by methods known pert: DE 3,218,121A; Epstein et al., 1985, "Proc. Natl. Acad. Sci. USA" 82: 3688–3692; Hwang et al., 1980, "Proc. Natl. Acad. Sci. USA" 77: 4030–4034; EP 52322A; EP 36676A; EP 88046A; EP 143949A; EP 142641A; Japanese patent application 83-118008; U.S. Pat. Nos. 4,485,045 and 4,544, 545; and EP 102,324A. Ordinarily the liposomes are of the small (about 200–800 Angstroms) unilamelar type in which the lipid content is greater than about 30 mol. % cholesterol, the selected proportion being adjusted for the optimal NT-4 therapy.

An effective amount of a molecule of the present invention to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage might range from about 1 $\mu$g/kg to up to 100 mg/kg or more, depending on the factors mentioned above. Typically, the clinician will administer a molecule of the present invention until a dosage is reached that provides the required biological effect. The progress of this therapy is easily monitored by conventional assay techniques. If the purpose of the treatment is weight reduction, the therapy is normally continued until a desired body weight is reached.

The invention will be further illustrated by the following non-limiting examples.

EXAMPLE 1

Expression of OB-immunoadhesins

Using protein engineering techniques, the human OB protein was expressed as a fusion with the hinge, CH2 and CH3 domains of IgG-1. DNA constructs encoding the chimera of the human OB protein and IgG-1 Fc domains were made with the Fc region clones of human IgG-1. Human OB cDNA was obtained by PCR from human fat cell dscDNA (Clontech Buick-Clone cDNA product). The source of the IgG-1 cDNA was the plasmid pBSSK-CH$_2$CH$_3$. The chimera contained the coding sequence of the full length OB protein (amino acids 1–167 in FIG. 5) and human IgG-1 sequences beginning at aspartic acid 216 (taking amino acid 114 as the first residue of the heavy chain constant region (Kabat et al., *Sequences of Proteins of Immunological Interest* 4th ed. [1987]), which is the first residue of the IgG-1 hinge after the cysteine residue involved in heavy-light chain bonding, and ending with residues 441 to include the CH2 and CH3 Fc domains of IgG-1. There was an insert of codons for three amino acids (GlyValThr) between the OB and IgG-1 coding sequences. If necessary, this short linker sequence can easily be deleted, for example by site directed deletion mutagenesis, to create an exact junction between the coding sequences of the OB protein and the IgG-1 hinge region. The coding sequence of the OB-IgG-1 immunoadhesin was subcloned into the pRK5-based vector pRK5tk-neo which contains a neomycine selectable marker, for transient expression in 293 cells using the calcium phosphate technique (Suva et al., *Science* 237, 893–896 [1987]). 293 cells were cultured in HAM's : Low Glucose DMEM medium (50:50), containing 10% FBS and 2 mM L-G1n. For purification of OB-IgG-1 chimeras, cells were changed to serum free production medium PS24 the day after transfection and media collected after three days. The culture media was filtered.

The filtered 293 cell supernatant (400 ml) containing recombinant human OB-IgG-1 was made 1 mM in phenyl-methylsulfonyl fluoride and 2 $\mu$g/ml in aprotinin. This material was loaded at 4° C. onto a 1×4.5 cm Protein A agarose column (Pierce catalog # 20365) equilibrated in 100 mM HEPES pH 8. The flow rate was 75 ml/h. Once the sample was loaded, the column was washed with equilibration buffer until the A$_{280}$ reached baseline. The OB-IgG-1 protein was eluted with 3.5 M MgCl$_2$+2% glycerol (unbuffered) at a flow rate of 15 ml/h. The eluate was collected with occasional mixing into 10 ml of 100 mM HEPES pH 8 to reduce the MgCl$_2$ concentration by approximately one-half and to raise the pH. The eluted protein was then dialyzed into phosphate buffered saline, concentrated, sterile filtered and stored either at 4° C. or frozen at −70 ° C. The OB-IgG-1 immunoadhesin prepared by this method is estimated by SDS-PAGE to be greater than 90% pure.

EXAMPLE 2

Animal Studies

A. Materials and Methods

OB protein Production—Murine OB cDNA was obtained by PCR from an adipocyte cDNA library using primers based on the sequence of Zhang et al., supra. Mature OB protein (amino acids 22–167) was expressed in *E. coli* by inserting the OB coding sequence in frame with the secretion sequence of the *E. coli* heat-stable enterotoxin II, downstream of the *E. coli* alkaline phosphatase promoter. Chang et al., *Gene* 55, 189–96 (1987). After cell lysis, the insoluble fraction was solubilized in 8 M urea buffer pH 8.35 in the presence of 25 mM DTT. Reduced OB protein was purified by size exclusion and reverse phase HPLC, then refolded in the presence of glutathione. Refolded OB protein was purified by reverse phase HPLC and analyzed by SDS-PAGE and amino acid and mass spectrometry analyses.

Preparation of PEG-hOB—The PEG derivatives of the human OB protein can be prepared essentially following the aldehyde chemistry described in EP 372,752 published Jun. 13, 1990.

Animal Studies—All manipulations involving animals were reviewed and approved by Genentech's Institutional Animal Care and Use Committee. Seven to eight week-old genetically obese C57BI/6J-ob/ob (ob/ob) female mice were purchase from Jackson Labs (Bar Harbor, Me.). Lean female mice of the same genetic background (C57BI/6) were purchased from Harlan Sprague Dawley (Hollister, Calif.). Mice were housed in groups 3–6 with ad libitum access to water and standard mouse chow (Purina 5010; Purina Mills, Richmond, Ind.) in a temperature-, humidity- and light-controlled (lights on at 06:00 h, of at 18:00 h) colony room.

Miniosmotic pumps (Alzet model 2002; Alza Corp., Palo Alto, Calif.) were filled with purified recombinant OB protein (100 $\mu$g/kg/day) in sterile phosphate-buffered saline (PBS) or PBS alone under sterile conditions following manufacturer's instructions and incubated overnight in sterile saline at room temperature prior to implantation into mice. Mice were anesthetized with ketamine/xylazine, and miniosmotic pumps were implanted subcutaneously in the midscapular region. Daily subcutaneous injections of purified recombinant OB protein, hOB-IgG-1 fusion protein or PBS were made into the midscapular region of conscious mice. Injections were performed within one hour of lights out. The body weight of each mouse (to the nearest 0.1 gram) and the weight of the food contained in the food bin in each cage (to the nearest 0.1 gram) were recorded within one hour of lights out every one to two days. The data are depicted as the mean±SEM. The number of animals is as described below and in the Figure legends.

B. Results with Continuous Subcutaneous Infusion of OB Protein

Lean female mice were treated with murine OB protein either as a continuous subcutaneous infusion or daily subcutaneous injections. The results are shown in FIG. 1. The upper chart shows that the OB protein is significantly more effective in reducing body weight when delivered as a continuous infusion than when the same dose is delivered in the form of daily subcutaneous injections. The bottom chart shows the same difference in the ability of the OB protein to reduce adipose tissue weight.

C. Results with the OB-IgG-1 Chimera

Obese female ob/ob mice were treated with human OB protein or with the human OB-IgG-1 chimera. The data are shown in FIG. 2. The data presented in the top chart demonstrate that the hOB-IgG-1 fusion protein is more potent than the native hOB protein at reducing body weight, when both proteins are administered similarly by daily subcutaneous infusion. It is noted that the increase in potency would be even more expressed, if the data were converted to molar amounts, as only about one third of the OB-IgG-1 chimera comes from the OB protein. The data further confirm the previous observation that continuous subcutaneous infusion (pump) or the hOB protein is more effective than daily subcutaneous injections (inj) at reducing body weight.

The data shown at the bottom chart of FIG. 2 show that the hOB-IgG-1 fusion protein substantially reduced food intake. This result was unexpected as it was assumed that the fusion protein would be too large to cross the blood-brain barrier and exert its effect.

Obese (ob/ob) female mice were treated with either hOB or the hOB-IgG-1 chimera by daily subcutaneous injections for 7 days. The data shown in FIG. 3 again demonstrate that the chimera is more effective than the native hOB protein at reducing body weight (top) and food intake (bottom).

D. Results with PEG-hOB

Obese female ob/ob mice were treated with human OB protein or with PEG derivatives of human OB. The data are shown in FIG. 4. The data presented in the top chart demonstrate that PEG-hOB is more potent than the native hOB protein at reducing body weight, when both proteins are administered similarly by daily subcutaneous infusion. It is noted that the increase in potency would be even more expressed, if the data were converted to molar amounts.

The data shown at the bottom chart of FIG. 4 show that the PEG-hOB proteins were substantially more effective in reducing food intake than unmodified native hOB.

While the invention has been illustrated by way of examples, the scope of the invention is not so limited. It will be understood that further modifications and variations are possible without diverting from the overall concept of the invention. All such modifications are intended to be within the scope of the present invention.

All references cited throughout the specification, including the examples, and the references cited therein are hereby expressly incorporated by reference.

What is claimed is:

1. A derivative of an obesity (OB) protein having a longer plasma half-life and/or slower clearance and greater potency than a native OB protein, comprising an OB protein amino acid sequence having at least 85% amino acid sequence identity with a native OB protein represented by the amino acid sequence between the N-terminus and the cysteine (Cys) at position 167 of SEQ ID NO: 2, covalently bonded to a nonproteinaceous polymer, wherein said derivative is capable of reducing body weight and/or food intake in an individual.

2. The derivative of claim 1 comprising the amino acid sequence of a native human OB protein represented by the amino acid sequence between the N-terminus and the cysteine (Cys) at position 167 of SEQ ID NO: 2.

3. The derivative of claim 1 wherein said OB protein amino acid sequence is fused to an immunoglobulin sequence.

4. The derivative of claim 3 wherein the nonproteinaceous polymer is polyethylene glycol (PEG).

5. A composition for the treatment of obesity, comprising an effective amount of an OB derivative of claim 1.

6. The derivative of claim 4 wherein said immunoglobulin sequence is a constant domain sequence.

7. The derivative of claim 6 wherein said OB protein is a native human OB protein represented by the amino acid sequence between the N-terminus and the cysteine (Cys) at position 167 of SEQ ID NO: 2.

8. The derivative of claim 7 wherein two OB polypeptide-IgG heavy chain fusions are linked to each other by at least one disulfide bond to yield a homodimeric immunoglobulin-like structure.

9. The derivative of claim 8 wherein at least one of said OB polypeptide-IgG heavy chain fusions comprises an immunoglobulin light chain, which is disulfide-linked to said OB polypeptide-IgG heavy chain fusion.

10. A composition for the treatment of obesity comprising an effective amount of a derivative of claim 4 in association with a pharmaceutically acceptable carrier.

11. The derivative of claim 1 wherein said nonproteinaceous polymer is polyethylene glycol (PEG).

12. A composition for the treatment of obesity, comprising an effective amount of an OB derivative of claim 3.

13. A composition for the treatment of obesity, comprising an effective amount of an OB derivative of claim 4.

14. A composition for the treatment of obesity comprising an effective amount of a derivative of claim 1 in association with a pharmaceutically acceptable carrier.

15. The derivative of claim 7 comprising a native mature OB protein fused to the C-terminus of an immunoglobulin heavy chain constant domain sequence.

16. The derivative of claim 15 wherein said OB protein amino acid sequence is fused to the hinge, CH2 and CH3 regions of the constant domain of an IgG heavy chain.

17. The derivative of claim 15 wherein said OB protein amino acid sequence is fused to the CH1, hinge, CH2 and CH3 regions of the constant domain of an IgG heavy chain.

18. A derivative of an obesity (OB) protein having a longer half-life and/or slower clearance and greater potency than a native OB protein amino acid sequence encoded by nucleic acid hybridizing under stringent conditions to the complement of a nucleic acid encoding a native OB protein represented by the amino acid sequence between the N-terminus and the cysteine (Cys) at position 167 of SEQ ID NO: 2, covalently bonded to a nonproteinaceous polymer, wherein said stringent conditions are hybridization in 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., followed with washed at 42° C. in 0.2×SSC and 0.1% SDS, and wherein said derivative is capable of reducing body weight and/or food intake in an individual.

19. The derivative of claim 18 wherein said nonproteinaceous polymer is polyethylene glycol (PEG).

20. The derivative of claim 19 wherein said OB protein is fused to an immunoglobulin constant domain sequence.

21. The derivative of claim 20 wherein said OB protein is fused to the hinge, CH2 and CH3 regions of the constant domain of an IgG heavy chain.

22. The derivative of claim 20 wherein said OB protein is fused to the CH1, hinge, CH2 and CH3 regions of the constant domain of an IgG heavy chain.

23. The derivative of claim 2 wherein the nonproteinaceous polymer is polyethylene glycol (PEG).

24. A composition for the treatment of obesity comprising an effective amount of a derivative of claim 7 in association with a pharmaceutically acceptable carrier.

25. A composition for the treatment of obesity, comprising an effective amount of an OB derivative of claim 7.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 7127 base pairs
      (B) TYPE: Nucleic Acid
      (C) STRANDEDNESS: Double
      (D) TOPOLOGY: Linear (xi) SEQUENCE DESCRIPTION: SEQ ID NO:1:

```
TTCGAGCTCG CCCGACATTG ATTATTGACT AGTTATTAAT AGTAATCAAT          50

TACGGGGTCA TTAGTTCATA GCCCATATAT GGAGTTCCGC GTTACATAAC         100

TTACGGTAAA TGGCCCGCCT GGCTGACCGC CCAACGACCC CCGCCCATTG         150

ACGTCAATAA TGACGTATGT TCCCATAGTA ACGCCAATAG GGACTTTCCA         200

TTGACGTCAA TGGGTGGAGT ATTTACGGTA AACTGCCCAC TTGGCAGTAC         250

ATCAAGTGTA TCATATGCCA AGTACGCCCC CTATTGACGT CAATGACGGT         300

AAATGGCCCG CCTGGCATTA TGCCCAGTAC ATGACCTTAT GGGACTTTCC         350

TACTTGGCAG TACATCTACG TATTAGTCAT CGCTATTACC ATGGTGATGC         400
```

```
GGTTTTGGCA GTACATCAAT GGGCGTGGAT AGCGGTTTGA CTCACGGGGA      450

TTTCCAAGTC TCCACCCCAT TGACGTCAAT GGGAGTTTGT TTTGGCACCA      500

AAATCAACGG GACTTTCCAA AATGTCGTAA CAACTCCGCC CCATTGACGC      550

AAATGGGCGG TAGGCGTGTA CGGTGGGAGG TCTATATAAG CAGAGCTCGT      600

TTAGTGAACC GTCAGATCGC CTGGAGACGC CATCCACGCT GTTTTGACCT      650

CCATAGAAGA CACCGGGACC GATCCAGCCT CCGCGGCCGG GAACGGTGCA      700

TTGGAACGCG GATTCCCCGT GCCAAGAGTG ACGTAAGTAC CGCCTATAGA      750

GTCTATAGGC CCACCCCCTT GGCTTCGTTA GAACGCGGCT ACAATTAATA      800

CATAACCTTA TGTATCATAC ACATACGATT TAGGTGACAC TATAGAATAA      850

CATCCACTTT GCCTTTCTCT CCACAGGTGT CCACTCCCAG GTCCAACTGC      900

ACCTCGGTTC TATCGATATG CATTGGGGAA CCCTGTGCGG ATTCTTGTGG      950

CTTTGGCCCT ATCTTTTCTA TGTCCAAGCT GTGCCCATCC AAAAAGTCCA      1000

AGATGACACC AAAACCCTCA TCAAGACAAT TGTCACCAGG ATCAATGACA      1050

TTTCACACAC GCAGTCAGTC TCCTCCAAAC AGAAAGTCAC CGGTTTGGAC      1100

TTCATTCCTG GGCTCCACCC CATCCTGACC TTATCCAAGA TGGACCAGAC      1150

ACTGGCAGTC TACCAACAGA TCCTCACCAG TATGCCTTCC AGAAACGTGA      1200

TCCAAATATC CAACGACCTG GAGAACCTCC GGGATCTTCT TCACGTGCTG      1250

GCCTTCTCTA AGAGCTGCCA CTTGCCCTGG GCCAGTGGCC TGGAGACCTT      1300

GGACAGCCTG GGGGGTGTCC TGGAAGCTTC AGGCTACTCC ACAGAGGTGG      1350

TGGCCCTGAG CAGGCTGCAG GGGTCTCTGC AGGACATGCT GTGGCAGCTG      1400

GACCTCAGCC CTGGGTGCGG GGTCACCGAC AAAACTCACA CATGCCCACC      1450

GTGCCCAGCA CCTGAACTCC TGGGGGGACC GTCAGTCTTC CTCTTCCCCC      1500

CAAAACCCAA GGACACCCTC ATGATCTCCC GGACCCCTGA GGTCACATGC      1550

GTGGTGGTGG ACGTGAGCCA CGAAGACCCT GAGGTCAAGT TCAACTGGTA      1600

CGTGGACGGC GTGGAGGTGC ATAATGCCAA GACAAAGCCG CGGGAGGAGC      1650

AGTACAACAG CACGTACCGT GTGGTCAGCG TCCTCACCGT CCTGCACCAG      1700

GACTGGCTGA ATGGCAAGGA GTACAAGTGC AAGGTCTCCA ACAAAGCCCT      1750

CCCAGCCCCC ATCGAGAAAA CCATCTCCAA AGCCAAAGGG CAGCCCCGAG      1800

AACCACAGGT GTACACCCTG CCCCCATCCC GGGAAGAGAT GACCAAGAAC      1850

CAGGTCAGCC TGACCTGCCT GGTCAAAGGC TTCTATCCCA GCGACATCGC      1900

CGTGGAGTGG GAGAGCAATG GGCAGCCGGA GAACAACTAC AAGACCACGC      1950

CTCCCGTGCT GGACTCCGAC GGCTCCTTCT TCCTCTACAG CAAGCTCACC      2000

GTGGACAAGA GCAGGTGGCA GCAGGGGAAC GTCTTCTCAT GCTCCGTGAT      2050

GCATGAGGCT CTGCACAACC ACTACACGCA GAAGAGCCTC TCCCTGTCTC      2100

CGGGTAAATG AGTGCGACGG CCCTAGAGTC GACCTGCAGA AGCTTCTAGA      2150

GTCGACCTGC AGAAGCTTGG CCGCCATGGC CCAACTTGTT TATTGCAGCT      2200

TATAATGGTT ACAAATAAAG CAATAGCATC ACAAATTTCA CAAATAAAGC      2250

ATTTTTTTCA CTGCATTCTA GTTGTGGTTT GTCCAAACTC ATCAATGTAT      2300

CTTATCATGT CTGGATCGAT CGGGAATTAA TTCGGCGCAG CACCATGGCC      2350
```

```
TGAAATAACC TCTGAAAGAG GAACTTGGTT AGGTACCTTC TGAGGCGGAA      2400

AGAACCAGCT GTGGAATGTG TGTCAGTTAG GGTGTGGAAA GTCCCCAGGC      2450

TCCCCAGCAG GCAGAAGTAT GCAAAGCATG CATCTCAATT AGTCAGCAAC      2500

CAGGTGTGGA AAGTCCCCAG GCTCCCCAGC AGGCAGAAGT ATGCAAAGCA      2550

TGCATCTCAA TTAGTCAGCA ACCATAGTCC CGCCCCTAAC TCCGCCCATC      2600

CCGCCCCTAA CTCCGCCCAG TTCCGCCCAT TCTCCGCCCC ATGGCTGACT      2650

AATTTTTTTT ATTTATGCAG AGGCCGAGGC CGCCTCGGCC TCTGAGCTAT      2700

TCCAGAAGTA GTGAGGAGGC TTTTTTGGAG GCCTAGGCTT TTGCAAAAAG      2750

CTGTTAATTC GAACACGCAG ATGCAGTCGG GGCGGCGCGG TCCCAGGTCC      2800

ACTTCGCATA TTAAGGTGAC GCGTGTGGCC TCGAACACCG AGCGACCCTG      2850

CAGCGACCCG CTTAACAGCG TCAACAGCGT GCCGCAGATC TGATCAAGAG      2900

ACAGGATGAG GATCGTTTCG CATGATTGAA CAAGATGGAT TGCACGCAGG      2950

TTCTCCGGCC GCTTGGGTGG AGAGGCTATT CGGCTATGAC TGGGCACAAC      3000

AGACAATCGG CTGCTCTGAT GCCGCCGTGT TCCGGCTGTC AGCGCAGGGG      3050

CGCCCGGTTC TTTTTGTCAA GACCGACCTG TCCGGTGCCC TGAATGAACT      3100

GCAGGACGAG GCAGCGCGGC TATCGTGGCT GGCCACGACG GGCGTTCCTT      3150

GCGCAGCTGT GCTCGACGTT GTCACTGAAG CGGGAAGGGA CTGGCTGCTA      3200

TTGGGCGAAG TGCCGGGGCA GGATCTCCTG TCATCTCACC TTGCTCCTGC      3250

CGAGAAAGTA TCCATCATGG CTGATGCAAT GCGGCGGCTG CATACGCTTG      3300

ATCCGGCTAC CTGCCCATTC GACCACCAAG CGAAACATCG CATCGAGCGA      3350

GCACGTACTC GGATGGAAGC CGGTCTTGTC GATCAGGATG ATCTGGACGA      3400

AGAGCATCAG GGGCTCGCGC CAGCCGAACT GTTCGCCAGG CTCAAGGCGC      3450

GCATGCCCGA CGGCGAGGAT CTCGTCGTGA CCCATGGCGA TGCCTGCTTG      3500

CCGAATATCA TGGTGGAAAA TGGCCGCTTT TCTGGATTCA TCGACTGTGG      3550

CCGGCTGGGT GTGGCGGACC GCTATCAGGA CATAGCGTTG GCTACCCGTG      3600

ATATTGCTGA AGAGCTTGGC GGCGAATGGG CTGACCGCTT CCTCGTGCTT      3650

TACGGTATCG CCGCTCCCGA TTCGCAGCGC ATCGCCTTCT ATCGCCTTCT      3700

TGACGAGTTC TTCTGAGCGG GACTCTGGGG TTCGAAATGA CCGACCAAGC      3750

GACGCCCAAC CTGCCATCAC GAGATTTCGA TTCCACCGCC GCCTTCTATG      3800

AAAGGTTGGG CTTCGGAATC GTTTTCCGGG ACGCCGGCTG GATGATCCTC      3850

CAGCGCGGGG ATCTCATGCT GGAGTTCTTC GCCCACCCCG GGAGATGGGG      3900

GAGGCTAACT GAAACACGGA AGGAGACAAT ACCGGAAGGA ACCCGCGCTA      3950

TGACGGCAAT AAAAAGACAG AATAAAACGC ACGGGTGTTG GGTCGTTTGT      4000

TCATAAACGC GGGGTTCGGT CCCAGGGCTG GCACTCTGTC GATACCCCAC      4050

CGAGACCCCA TTGGGGCCAA TACGCCCGCG TTTCTTCCTT TTCCCCACCC      4100

CAACCCCCAA GTTCGGGTGA AGGCCCAGGG CTCGCAGCCA ACGTCGGGGC      4150

GGCAAGCCCG CCATAGCCAC GGGCCCCGTG GGTTAGGGAC GGGGTCCCCC      4200

ATGGGGAATG GTTTATGGTT CGTGGGGGTT ATTCTTTTGG GCGTTGCGTG      4250

GGGTCAGGTC CACGACTGGA CTGAGCAGAC AGACCCATGG TTTTTGGATG      4300

GCCTGGGCAT GGACCGCATG TACTGGCGCG ACACGAACAC CGGGCGTCTG      4350
```

```
TGGCTGCCAA ACACCCCCGA CCCCCAAAAA CCACCGCGCG GATTTCTGGC      4400

GCCGCCGGAC GAACTAAACC TGACTACGGC ATCTCTGCCC CTTCTTCGCT      4450

GGTACGAGGA GCGCTTTTGT TTTGTATTGG TCACCACGGC CGAGTTTCCG      4500

CGGGACCCCG GCCAGGGCAC CTGTCCTACG AGTTGCATGA TAAAGAAGAC      4550

AGTCATAAGT GCGGCGACGA TAGTCATGCC CCGCGCCCAC CGGAAGGAGC      4600

TGACTGGGTT GAAGGCTCTC AAGGGCATCG GTCGAGCGGC CGCATCAAAG      4650

CAACCATAGT ACGCGCCCTG TAGCGGCGCA TTAAGCGCGG CGGGTGTGGT      4700

GGTTACGCGC AGCGTGACCG CTACACTTGC CAGCGCCCTA GCGCCCGCTC      4750

CTTTCGCTTT CTTCCCTTCC TTTCTCGCCA CGTTCGCCGG CTTTCCCCGT      4800

CAAGCTCTAA ATCGGGGGCT CCCTTTAGGG TTCCGATTTA GTGCTTTACG      4850

GCACCTCGAC CCCAAAAAAC TTGATTTGGG TGATGGTTCA CGTAGTGGGC      4900

CATCGCCCTG ATAGACGGTT TTTCGCCCTT TGACGTTGGA GTCCACGTTC      4950

TTTAATAGTG GACTCTTGTT CCAAACTGGA ACAACACTCA ACCCTATCTC      5000

GGGCTATTCT TTTGATTTAT AAGGGATTTT GCCGATTTCG GCCTATTGGT      5050

TAAAAAATGA GCTGATTTAA CAAAAATTTA ACGCGAATTT TAACAAAATA      5100

TTAACGTTTA CAATTTTATG GTGCAGGCCT CGTGATACGC CTATTTTTAT      5150

AGGTTAATGT CATGATAATA ATGGTTTCTT AGACGTCAGG TGGCACTTTT      5200

CGGGGAAATG TGCGCGGAAC CCCTATTTGT TTATTTTTCT AAATACATTC      5250

AAATATGTAT CCGCTCATGA GACAATAACC CTGATAAATG CTTCAATAAT      5300

ATTGAAAAAG GAAGAGTATG AGTATTCAAC ATTTCCGTGT CGCCCTTATT      5350

CCCTTTTTTG CGGCATTTTG CCTTCCTGTT TTTGCTCACC CAGAAACGCT      5400

GGTGAAAGTA AAAGATGCTG AAGATCAGTT GGGTGCACGA GTGGGTTACA      5450

TCGAACTGGA TCTCAACAGC GGTAAGATCC TTGAGAGTTT TCGCCCCGAA      5500

GAACGTTTTC CAATGATGAG CACTTTTAAA GTTCTGCTAT GTGGCGCGGT      5550

ATTATCCCGT GATGACGCCG GGCAAGAGCA ACTCGGTCGC CGCATACACT      5600

ATTCTCAGAA TGACTTGGTT GAGTACTCAC CAGTCACAGA AAAGCATCTT      5650

ACGGATGGCA TGACAGTAAG AGAATTATGC AGTGCTGCCA TAACCATGAG      5700

TGATAACACT GCGGCCAACT TACTTCTGAC AACGATCGGA GGACCGAAGG      5750

AGCTAACCGC TTTTTTGCAC AACATGGGGG ATCATGTAAC TCGCCTTGAT      5800

CGTTGGGAAC CGGAGCTGAA TGAAGCCATA CCAAACGACG AGCGTGACAC      5850

CACGATGCCA GCAGCAATGG CAACAACGTT GCGCAAACTA TTAACTGGCG      5900

AACTACTTAC TCTAGCTTCC CGGCAACAAT TAATAGACTG GATGGAGGCG      5950

GATAAAGTTG CAGGACCACT TCTGCGCTCG GCCCTTCCGG CTGGCTGGTT      6000

TATTGCTGAT AAATCTGGAG CCGGTGAGCG TGGGTCTCGC GGTATCATTG      6050

CAGCACTGGG GCCAGATGGT AAGCCCTCCC GTATCGTAGT TATCTACACG      6100

ACGGGGAGTC AGGCAACTAT GGATGAACGA AATAGACAGA TCGCTGAGAT      6150

AGGTGCCTCA CTGATTAAGC ATTGGTAACT GTCAGACCAA GTTTACTCAT      6200

ATATACTTTA GATTGATTTA AAACTTCATT TTTAATTTAA AAGGATCTAG      6250

GTGAAGATCC TTTTTGATAA TCTCATGACC AAAATCCCTT AACGTGAGTT      6300
```

-continued

```
TTCGTTCCAC TGAGCGTCAG ACCCCGTAGA AAAGATCAAA GGATCTTCTT      6350

GAGATCCTTT TTTTCTGCGC GTAATCTGCT GCTTGCAAAC AAAAAAACCA      6400

CCGCTACCAG CGGTGGTTTG TTTGCCGGAT CAAGAGCTAC CAACTCTTTT      6450

TCCGAAGGTA ACTGGCTTCA GCAGAGCGCA GATACCAAAT ACTGTCCTTC      6500

TAGTGTAGCC GTAGTTAGGC CACCACTTCA AGAACTCTGT AGCACCGCCT      6550

ACATACCTCG CTCTGCTAAT CCTGTTACCA GTGGCTGCTG CCAGTGGCGA      6600

TAAGTCGTGT CTTACCGGGT TGGACTCAAG ACGATAGTTA CCGGATAAGG      6650

CGCAGCGGTC GGGCTGAACG GGGGGTTCGT GCACACAGCC AGCTTGGAG       6700

CGAACGACCT ACACCGAACT GAGATACCTA CAGCGTGAGC ATTGAGAAAG      6750

CGCCACGCTT CCCGAAGGGA GAAAGGCGGA CAGGTATCCG GTAAGCGGCA      6800

GGGTCGGAAC AGGAGAGCGC ACGAGGGAGC TTCCAGGGGG AAACGCCTGG      6850

TATCTTTATA GTCCTGTCGG GTTTCGCCAC CTCTGACTTG AGCGTCGATT      6900

TTTGTGATGC TCGTCAGGGG GGCGGAGCCT ATGGAAAAAC GCCAGCTGGC      6950

ACGACAGGTT TCCCGACTGG AAAGCGGGCA GTGAGCGCAA CGCAATTAAT      7000

GTGAGTTACC TCACTCATTA GGCACCCCAG GCTTTACACT TTATGCTTCC      7050

GGCTCGTATG TTGTGTGGAA TTGTGAGCGG ATAACAATTT CACACAGGAA      7100

ACAGCTATGA CCATGATTAC GAATTAA                              7127
```

(2) INFORMATION FOR SEQ ID NO:2:

(i) SEQUENCE CHARACTERISTICS:
        (A) LENGTH: 397 amino acids
        (B) TYPE: Amino Acid
        (D) TOPOLOGY: Linear (xi) SEQUENCE DESCRIPTION: SEQ ID NO:2:

```
Met His Trp Gly Thr Leu Cys Gly Phe Leu Trp Leu Trp Pro Tyr
 1               5                  10                  15

Leu Phe Tyr Val Gln Ala Val Pro Ile Gln Lys Val Gln Asp Asp
                20                  25                  30

Thr Lys Thr Leu Ile Lys Thr Ile Val Thr Arg Ile Asn Asp Ile
                35                  40                  45

Ser His Thr Gln Ser Val Ser Ser Lys Gln Lys Val Thr Gly Leu
                50                  55                  60

Asp Phe Ile Pro Gly Leu His Pro Ile Leu Thr Leu Ser Lys Met
                65                  70                  75

Asp Gln Thr Leu Ala Val Tyr Gln Gln Ile Leu Thr Ser Met Pro
                80                  85                  90

Ser Arg Asn Val Ile Gln Ile Ser Asn Asp Leu Glu Asn Leu Arg
                95                 100                 105

Asp Leu Leu His Val Leu Ala Phe Ser Lys Ser Cys His Leu Pro
               110                 115                 120

Trp Ala Ser Gly Leu Glu Thr Leu Asp Ser Leu Gly Gly Val Leu
               125                 130                 135

Glu Ala Ser Gly Tyr Ser Thr Glu Val Val Ala Leu Ser Arg Leu
               140                 145                 150

Gln Gly Ser Leu Gln Asp Met Leu Trp Gln Leu Asp Leu Ser Pro
               155                 160                 165

Gly Cys Gly Val Thr Asp Lys Thr His Thr Cys Pro Pro Cys Pro
               170                 175                 180
```

-continued

```
Ala Pro Glu Leu Leu Gly Gly Pro Ser Val Phe Leu Phe Pro Pro
                185             190              195

Lys Pro Lys Asp Thr Leu Met Ile Ser Arg Thr Pro Glu Val Thr
                200             205              210

Cys Val Val Asp Val Ser His Glu Asp Pro Glu Val Lys Phe
                215             220              225

Asn Trp Tyr Val Asp Gly Val Glu Val His Asn Ala Lys Thr Lys
                230             235              240

Pro Arg Glu Glu Gln Tyr Asn Ser Thr Tyr Arg Val Val Ser Val
                245             250              255

Leu Thr Val Leu His Gln Asp Trp Leu Asn Gly Lys Glu Tyr Lys
                260             265              270

Cys Lys Val Ser Asn Lys Ala Leu Pro Ala Pro Ile Glu Lys Thr
                275             280              285

Ile Ser Lys Ala Lys Gly Gln Pro Arg Glu Pro Gln Val Tyr Thr
                290             295              300

Leu Pro Pro Ser Arg Glu Glu Met Thr Lys Asn Gln Val Ser Leu
                305             310              315

Thr Cys Leu Val Lys Gly Phe Tyr Pro Ser Asp Ile Ala Val Glu
                320             325              330

Trp Glu Ser Asn Gly Gln Pro Glu Asn Asn Tyr Lys Thr Thr Pro
                335             340              345

Pro Val Leu Asp Ser Asp Gly Ser Phe Phe Leu Tyr Ser Lys Leu
                350             355              360

Thr Val Asp Lys Ser Arg Trp Gln Gln Gly Asn Val Phe Ser Cys
                365             370              375

Ser Val Met His Glu Ala Leu His Asn His Tyr Thr Gln Lys Ser
                380             385              390

Leu Ser Leu Ser Pro Gly Lys
                395     397
```